(12) United States Patent
Shachar et al.

(10) Patent No.: US 8,133,172 B2
(45) Date of Patent: Mar. 13, 2012

(54) BRAIN RETRACTOR APPARATUS FOR MEASURING AND PREDICTING ELECTROPHYSIOLOGICAL PARAMETERS

(75) Inventors: Josh Shachar, Santa Monica, CA (US); Thomas Chen, La Canada, CA (US); Leslie Farkas, Ojai, CA (US); Winston Wu, Alhambra, CA (US); Kyle Zimmerman, Los Angeles, CA (US); Moran Cerf, Los Angeles, CA (US); Bruce Marx, Ojai, CA (US); David Johnson, West Hollywood, CA (US); Laszlo Farkas, Ojai, CA (US)

(73) Assignee: Pharmaco-Kinesis Corporation, Inglewood, CA (US)

( * ) Notice: Subject to any disclaimer, the term of this patent is extended or adjusted under 35 U.S.C. 154(b) by 557 days.

(21) Appl. No.: 12/343,436

(22) Filed: Dec. 23, 2008

(65) Prior Publication Data
US 2010/0160737 A1  Jun. 24, 2010

(51) Int. Cl.
*A61B 1/32* (2006.01)

(52) U.S. Cl. ......................... 600/202; 600/544

(58) Field of Classification Search .................. 600/202, 600/544
See application file for complete search history.

(56) References Cited

U.S. PATENT DOCUMENTS

| | | | | |
|---|---|---|---|---|
| 3,888,117 A | * | 6/1975 | Lewis | 73/862.53 |
| 4,784,150 A | * | 11/1988 | Voorhies et al. | 600/473 |
| 4,945,896 A | * | 8/1990 | Gade | 600/202 |
| 5,456,254 A | * | 10/1995 | Pietroski et al. | 600/372 |
| 6,916,294 B2 | * | 7/2005 | Ayad | 600/587 |
| 7,153,279 B2 | * | 12/2006 | Ayad | 600/587 |
| 2009/0259106 A1 | * | 10/2009 | Catapano et al. | 600/202 |
| 2010/0160737 A1 | * | 6/2010 | Shachar et al. | 600/202 |
| 2011/0043225 A1 | * | 2/2011 | Sullivan et al. | 324/658 |

* cited by examiner

*Primary Examiner* — Ralph Lewis
(74) *Attorney, Agent, or Firm* — Marcus C. Dawes; Daniel L. Dawes

(57) ABSTRACT

Described is a surgical system for monitoring a patient's condition during surgery. One aspect is a non-contact EEG sensor. The non-contact EEG sensor can be used to predict the onset of physiological disorders. Another aspect includes the use of a plurality of pressure sensors to determine the pressure applied by retractors on the patient, including the brain and other organs.

16 Claims, 17 Drawing Sheets

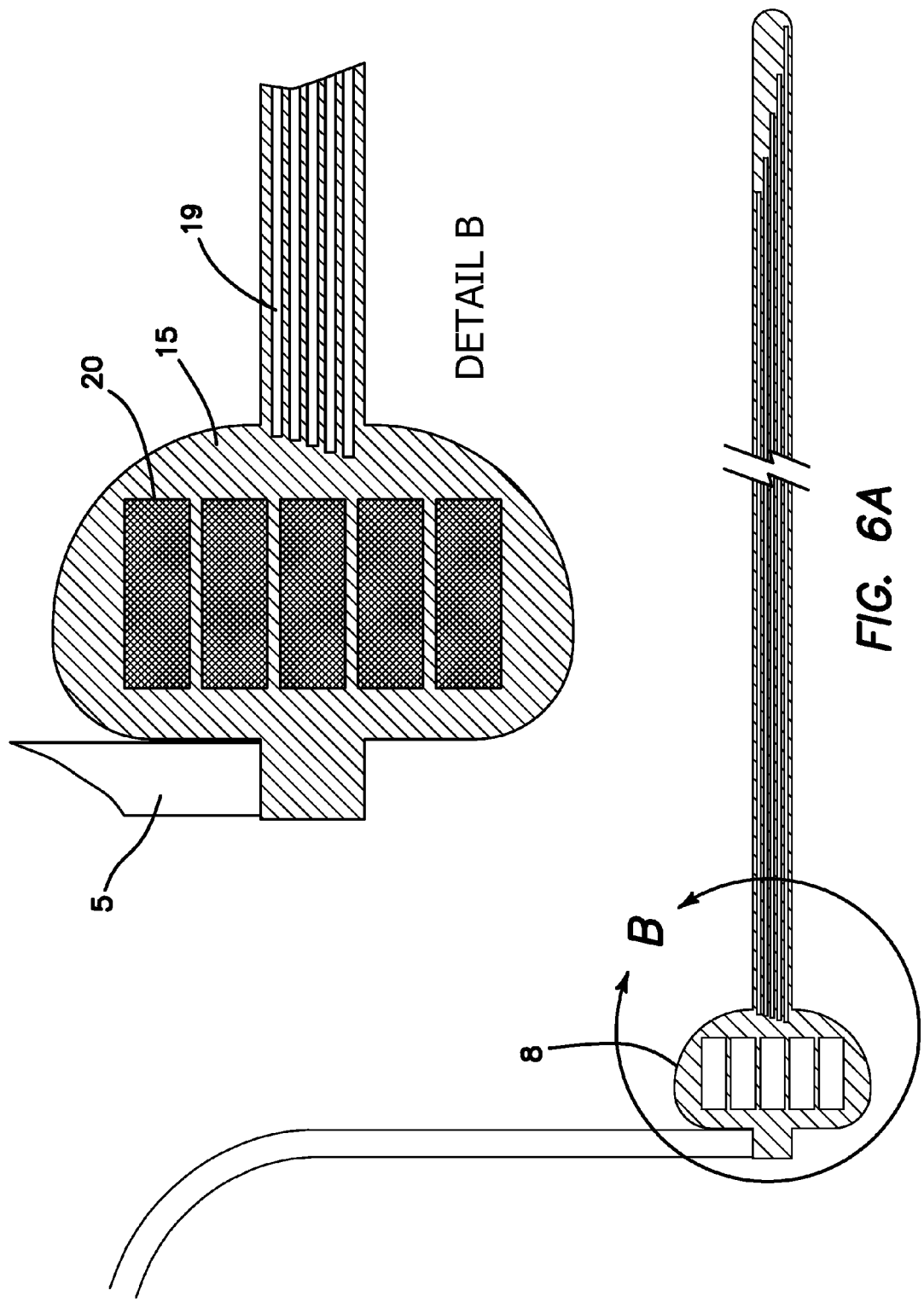

BRAIN RETRACTOR APPARATUS FOR MEASURING AND PREDICTING ELECTROPHYSIOLOGICAL PARAMETERS

FIELD OF THE INVENTION

This invention relates generally to surgical retractors and more particularly to a surgical retractor assembly having an embedded sensor array for detecting and predicting local electrophysiological parameters such as electroencephalographic (EEG) signal, pressure beneath the retractor blade, and temperature activity of the tissue, and further for providing an early warning as to the viability of the underlying tissue during surgery and a monitoring system for displaying a signal representative of this activity.

BACKGROUND

Intracranial operations, such as those involving vascular malformations, aneurysms, and certain tumors, e.g., acoustic neurinomas or skull base tumors require intraoperative retraction of the normal brain in order to obtain surgical access to deep pathological intracranial lesions. In certain situations, such as subarachnoid hemorrhage from aneurysms or cerebral edema from a large brain tumor, not only is retraction needed for surgical access, but the brain itself is swollen from the pathology itself. This requires even more retraction in order to obtain the same surgical exposure that could have been obtained from a "relaxed" brain. In essence, brain retraction is a "necessary evil" in brain surgery. Brain retraction is needed to gain exposure, but undue pressure results in increased morbidity and even potential mortality. In order to obtain adequate operative exposure, a surgical instrument known as a retractor i.e. "soft brain retractor" or "self-retaining" retractor is used. The current technology that is used in the operating room is a passive metallic system. Brain retractors are currently made of steel and usually have tapered ends. They are typically attached to a "snake" which can be tightened at the attachment to a Mayfield head holder. They come in various shapes and sizes, are "malleable" in that they can be bent to various angles depending on the procedure at hand, and can be detached and repositioned at the surgeon's discretion. The neurosurgeon places the retractor on the brain, and periodically "loosens" it or places it on another part of the brain that requires retraction. There is no feedback that is given to the surgeon on whether a local region of the brain is injured or has the potential of suffering injury. As a result, a portion of the brain can be retracted for a period of time (up to several hours) with resultant retractor injury from direct local pressure on the brain tissue, exerting local cytotoxicity or regional ischemia. It is estimated that up to 5% of intracranial aneurysm surgery, and 10% of skull base surgeries result in retraction injury to the brain.

Although different types of brain retractors with various configurations of neuro monitoring have been devised, none of them have been popularized for generaluse. Innovations in brain retractors have typically focused on the brain retractor material, the degree angulation's that can be achieved, and the neurophysiological monitoring that is applied adjacent to the retractor. Some investigators have advocated titanium, for the retractor blade, carbon grade (for lucency), and placement of gelatin sponges as buffer between the brain and the retractor. Others have advocated the use of thinner diameter blades to minimize focal brain injury; thin tapered blades are currently the favored shape. Various neurophysiological probes have been placed adjacent to the retractors to measure the effects of the retractor blades on the adjacent brain. Various parameters have been measured including EEG, evoked potentials (EP), focal cerebral blood flow measurements, and strain gauge.

The following is a summary of the prior art that has been filed on brain retractors.

A comprehensive study of the subject introduced by Andrews R. M.D. & Bringas J. Titled *A Brain Retraction and Recommendations for Minimizing Intraoperative Brain Injury Neurosurgery* 36(6) December 1993, p 1052-1064 survey the use of surgical retractor and the problem of brain retraction injury. In the efforts of identifying the incidence of brain retraction injury the study review the existing art and a critical approach to the technique and procedures employed. As a result of the recommendations noted by the study, local real time electrophysiological sensing and monitoring with the capabilities of predicting the state of the tissue in the examination will improve the art of intracranial operations, while reducing injury and post operative morbidity.

Several methods have been developed to try to measure and report the pressure as well as EEG signals in order to alert or report the potential harmful conditions of too much pressure applied to the brain tissue by the retractor. The prior art listed below is representative of the efforts by the community of physician and inventors to reduce the percentage of injuries resulting from current practice.

McEwen, et al. in U.S. Pat. No. 5,201,325 teach an apparatus useful in surgery for holding retractors and other surgical instrumentation in a number of different positions required by a surgeon for the performance of a surgical procedure, including advanced sensing and regulation of retraction pressures and position; and incorporating a force amplification method to drive a locking mechanism in the supporting structure that utilizes a constrained, substantially incompressible, flexible solid material to yield a mechanism that is suitable for clinical use.

Larnard in U.S. Pat. No. 6,733,442 describe an invention "Accessory for surgical instrument" The device provides a surgical device for decreasing the trauma imposed on soft tissue by extended contact with a surgical device during a surgical procedure by thermally treating the tissue. To thermally treat the tissue, the surgical device can be configured to include a structure for enveloping and receiving at least a portion of the surgical device, where the structure is configured to control thermal energy transfer between the structure and the tissue.

Brockway, et al, U.S. Pat. No. 6,296,615 describe a Catheter with physiological sensor. The disclosed embodiments present improved catheters with physiological sensors. In one embodiment, the catheter includes a pressure transducer/electronics assembly connected to a pressure transmission catheter. The pressure transmission catheter includes a hollow tube made from a low compliance material. The distal end of the hollow tube is filled with a gel-like material or plug which acts as a barrier between the catheter liquid and the target fluid. The hollow tube is partially filled with a low viscosity liquid and is in fluid communication with the gel-like material and the pressure transducer. The pressure of the target fluid is transmitted to the liquid in the hollow tube through the gel-like material and/or the wall of the distal tip and is fluidically transmitted to the pressure transducer. The pressure transmission catheter is capable of being inserted into a vessel lumen or inserted into a lumen of a therapeutic or diagnostic catheter for biomedical applications. This provides the ability to directly measure the pressure effects of the treatment catheter. In another embodiment, the distal end of the pressure transmission catheter may be electrically conductive so as to detect and transmit an electric signal. Thus, in this embodiment, the catheter can be used to detect a physiological signal.

Huey, et al. in U.S. Pat. No. 6,104,941 describe a physiological sensor with a combination of a pressure control and a catheter including an elongate member, a sensor mounted on the catheter and adapted to be placed in pressure engagement with tissue for sensing signals resulting from physiological phenomena and an expandable member mounted on the elongate member for maintaining the sensor in contact with the tissue. A pressure source is connected to the expandable member for maintaining the expandable member inflated and a pressure controller coupled to the expandable member for maintaining the contact pressure between the sensor and the tissue within pre selected limits.

Fischell et al. in U.S. Pat. No. 6,061,593 disclosed an EEG d-c voltage shift as a means for detecting the onset of a neurological event with a multiple electrode, closed-loop system for the treatment of certain neurological disorders such as epilepsy, migraine headaches and Parkinson's disease. Specifically, the present invention combines a multi-electrode array with sophisticated signal processing techniques to achieve reliable detection of the onset of a neurological event (such as an epileptic seizure or migraine headache) typically originating from a focus of limited spatial extent within the brain. It is highly desirable to detect an epileptic seizure at least 5 seconds before the onset of clinical symptoms. Since there is often a d-c shift in the EEG voltage more than 5 seconds before the seizure, disclosed herein is a means for utilizing the d-c shift of the EEG for early detection of the seizure.

Mayevsky in U.S. Pat. No. 5,916,171 describe a Tissue monitor A single signal-single probe multi parameter analyzer apparatus for monitoring various parameters of the identical volume element of body tissue, which includes an input signal generator, a single signal guide which transmits input signal in, and transmits output signal out, constituting a single signal-single probe, a signal splitter which splits output signal into two or more parts, filters which separate various components of output signal, detectors which measure the different components of the output signal, a computer and an analog to digital converter; and algorithms to evaluate the data.

Chappuis in U.S. Pat. No. 5,769,781 describes Protector retractor with a handle which carries a dry cell battery which supplies current to a microprocessor which receives signals from a sensor on the end of a bill carried by a staff which projects from the handle. The signal to the microprocessor is converted to a display on the handle. The display has alarms to indicate when the retractor applies too much force to a spinal cord or when the force has been applied for too long a time.

Ayad in U.S. Pat. No. 7,153,279 describe Brain retraction sensor with an electrode device is disclosed comprising a deformable envelope, further comprising recording electrodes and a pressure recording port. The device allows for monitoring of brain retraction pressure and local cortical electrical activity including DC potential, as well as redistribution of the force applied during retraction and cushioning of the rigid edges of the brain retractor, thereby diminishing the chance of focal brain injury during surgery. Retraction pressure recorded is equal over the full area of contact. A means is disclosed for optional evacuation of air from the system to improve accuracy and fidelity of the pressure measurements. Local brain hypothermia may be induced via the bladder and attached catheter, thereby providing additional neuro-protection during brain retraction. The device also allows for measurement of intracranial pressure, DC potential, EEG and, optionally, other physiologic parameters in epileptic and severe head trauma patients for management of edema and injury.

In the ensuing paragraphs we highlight the fact that cellular etiology do provide us with electrophysiological indications that if captured early within the time domain of the detecting procedure will enable the measuring system to predict and alert the surgeon of the impending damage to the tissue in question. We further instruct in this application that the use of the apparatus proposed solve these and other problems associated with intracranial intervention, and by the consistent application of the methods and embodiments of this invention a robust predictive algorithm is enabled so as to dramatically reduce the incidence of morbidity and mortality associated with the use of brain retractor. While use of these retractors, often for several hours, is necessary to expose the surgical site, surgeons and particularly neurosurgeons have worried that the pressure exerted on the delicate neuralgic tissues can cause irreversible damage thereto. As reported by the medical practitioner, the neurosurgeon has traditionally relied on his experience and tactile sensory outputs in setting a safe level of retractor pressure. This may prevent physical crushing or mechanical damage of the tissues, but of greater concern is the possibility of severely compromised local blood flow under the retractor tip. This reduced blood flow could lead to oxygen starvation of the tissue cells called cerebral ischemia. This type of damage cannot be visually detected by the surgeon, even with the use of a microscope, hence the use of varieties of sensor platform to detect and alert the physician of the impending mechanical damage resulting in ischemia.

Further evidence of physiological parameters such as EEG variations due to ischemia have been shown to correlate between brain retractor pressure and EEG wave form characteristics which could prove useful in evaluating or predicting damage caused by retractor pressure. Voorhies et al. U.S. Pat. No. 4,784,150 summarizes the findings of research conducted by Tolonen and Sulg (1981) which found that the power in the delta band (0.0 to 4.69 Hz) of the EEG power spectrum correlated inversely with regional cerebral blood flow, such that an increase of EEG power in this band could warn of impending ischemic damage. These parameters are exploited by this invention in the process of improving the predictive qualities of the proposed algorithm. Further reported by Behrens et al., "Subdural and Depth Electrodes in the Pre surgical Evaluation of Epilepsy" Acta Neurochir (1994) 128:84-87 that While knowing the amount of pressure applied, the variables that influence the threshold sensitivity of the brain to different degrees of retraction include the depth of anesthesia, systemic parameters such as blood oxygen and carbon dioxide levels, and the specific area of the brain being retracted. As a result, electrophysiological monitoring of the brain can give a more accurate indication of when the threshold for injury is being approached by analyzing the complex signal-patterns of the electroencephalogram (EEG) and somatosensory evoked potentials (SSEP). In the current method of measuring EEG, the electrodes commonly used depend on the position and placement on the scalp. Because of this, electrodes can only be placed to the extent that they do not interfere with the sterile surgical field, and obviously cannot be placed in the area of the craniotomy, which it is precisely the part of the brain that needs to be monitored. The invention and its embodiments as featured by the use of an intraoperative integrated MOSFET Sensor Array solve this and other problem of local definition of reporting on essential physiological parameters, without the compromise noted in the prior art.

Additional evidence of the need to record, report and predict the data generated by the EEG & SSEP signals while first establishing the retraction pressure of 30 mm Hg, (within the range used in clinical neurosurgery) has usually results in a 50% decrement in electric potential amplitude within 15 minutes of beginning retraction, (Andrews R J, Muto R P Neurol Res 14:12-18 1982). This facts and others will assist the proposed invention in setting the limits necessary for safe retraction pressure while maintaining an adequate separation of the tissue in question, this task and others is addressed by the use of "Look-Up Tables", which reside in memory bank of the proposed apparatus.

The need to supplement the pressure monitoring and reporting of the brain retractor in order to reduce retraction injury by the use of local EEG monitoring is further supported by the experimental work conducted by Williams C. published under PCT WO 95/35060. Whereby the underlying mechanism of impedance variations within nervous tissue, (wherein the presence of myelinated tracts giving a relatively low conductivity), results in conductivity change of the tissue rises as the ion-containing, extra cellular fluid which provides for more conduction paths. Typical values for white matter are 700 ohm-cm; for grey matter, 300 ohm-cm. The skull is typically 5000 ohm-cm. This variation of conductivity in different tissues are the main reason why the bioelectric potentials need to be measured locally, so as to avoid the SNR (Signal to Noise Ratio) distortion associated with global EEG indications as the primary tool for predicting the anticipated event of ischemia due to over pressure, or prolonged retraction of the apparatus. In addition to differences in local conductivity between gray and white matter, the measurements from global EEG measurements are further compromised secondary to the use of medications administered at the time of surgery such as anesthetic agents, dexamethasone (given to reduce brain swelling), mannitol (an osmotic agent used for diuresis), and lasix (osmotic agent used for diuresis). Other drugs such as intraoperative anticonvulsants (i.e. phenytoin or keppra) may cause distortions in local neurophysiology. The net result, cell swelling, is really a combination of retraction pressure, medications administered, and anesthesia. Cellular swelling affects both neurons and glial cells, of which neurophysiological changes are best appreciated on a local intraoperative EEG level rather a global scalp EEG. Therefore, these cellular changes due to metabolic assimilation of mechanical as well as chemical changes are mirrored by electrical manifestations, resulting in a state which this novel MOSFET apparatus, with its local EEG, detects. Moreover, these variations and prediction of the state of the cellular conditions and or viability relative to perfusion of blood as well as oxygenation is than reported to the surgeon via audio as well as visual messages.

In addition to external factors (i.e. retraction, anesthesia, medications), intrinsic intracranial pathology may result in intracellular and intercellular fluid accumulation, resulting in decrease in tissue conductivity, with increased impedance. These changes in the cellular structure are mapped and mirrored by the corresponding electrical characteristics of the cellular medium, hence providing the physical basis for the EEG local monitoring as a predictive tool for anticipating the condition of ischemia. The MOSFET Integrated EEG/Pressure & Temperature Sensor Array enable the physician to readily obtain impedance values of the measured tissue as well as EEG data so as to improve the predictable embodiments of the use of the proposed invention.

Additional parameter which correlate the mechanical pressure exerted by the brain retractor and EEG outputs was reported by Pronk and Simons (1982), concluding that the Hjorth time domain parameter of "mobility" where Short-time segments of duration 1 s or longer are analyzed and three parameters are computed. The first parameter is called activity $A^2=<y^2>$ and is simply the variance of the signal segment. The second parameter, called mobility Mx, is computed as the square root of the ratio of the activity of the first derivative of the signal to the activity of the (original) signal: $<(dy/dt)^2>/A^2$. The third parameter, called complexity or the form factor FF, is defined as the ratio of the mobility of the first derivative of the signal to the mobility of the signal itself: $C^2=<(d^2y/d^2t)^2>/A^2$ (Hjorth, 1970). Other techniques that can possibly be employed while applying the retractor with the apparatus noted by the invention are: Time Domain Parameters, Barlow Parameters Frequency Domain Parameter, FFT, Periodogram and the Hjorth parameters noted above. The processing of the local EEG with the analytical tools noted above, is supported by the proposed architecture as described by the accompanying figures.

The apparatus is further augmented with the necessary limits for safe retraction pressure and duration by the aid of look-up-tables 603.1, residing in the memory banks of microcontroller 603. The threshold and boundary conditions for the limits, are defined by algorithm and AI routines 603.2 forming the alerts loop 603.3.

Mechanical pressure placed on the tissue by the brain retractor will results in lower blood flow immediately beneath the retractor compared to the surrounding regions. Astrup et. al. 1981, have found that flow rates below 10 to 13 ml/100 gm/min lead to cell damage. It has been found that if the Mean Arterial Pressure (MAP) exceeds the Brain Retraction Pressure (BRP) by less than 70 mm Hg, the brain will be damaged (i.e., brain damage will occur if (MAP-BRP<70 mm Hg)). However, it has also been found that when the difference between BRP and MAP is greater than 100 mm Hg, the brain will typically recover completely (i.e., no lasting brain damage will occur when (MAP-BRP>100 mm Hg).

SUMMARY

Thus, to safeguard the brain during a lengthy surgery, it is desirable that the brain retractor be provided with a means for monitoring the EEG signal, pressure applied to the brain tissue, and temperature of the underlying brain tissue. Moreover, a warning system that warns the surgeon of EEG changes consistent with impending brain ischemia, MAP that exceeds BRP by less than 70 mm Hg, and temperature>38 degrees Celsius, would alert the surgeon to ease up on the brain retraction. In summary, none of the prior art discussed above provides a method and apparatus that sense, analyze, and reports the state of the local brain physiology underneath a retractor on a real time basis, enabling the surgeon and his staff to alter the impending state of ischemia from brain retraction, hence reducing the rate of neurological injury, while still employing the brain retractor for its intended purpose of enhancing exposure of the intracranial lesion to be surgically treated.

A surgical retractor assembly is provided according to the teachings of one embodiment of the present invention for retracting and holding soft body tissue such as brain tissue in a stationary retracted position while monitoring the viability of the soft body tissue underlying the retractor.

For example, a platform inserted and fitted over a smooth, generally flat, elongated blade such as for example soft brain spatula for deep area or Kuwana siliconized brain spatula, may be used in one embodiment.

In an embodiment, the retractor system includes the ability to process the data and provide a timely predictive algorithm so as to anticipate brain injury that may be irreversible.

In an embodiment, the brain retractor system is configured to detect and alert the physician of any impending ischemia or seizures during the course of the procedure. In an embodiment, the brain retractor system is configured to alert the physician to changes in the brain EEG patterns which may be indicative of potential accumulated damage to the brain. An ischemic or seizure state is clinically manifested by an involuntary alteration in behavior, movement, sensation, or consciousness. The cellular etiological changes underlying that state is reflected in clinical behaviors preceded and then accompanied by EEG alterations that include discharges of monomorphic (single-frequency) waveforms; polymorphic (multi-frequency) waveforms; spikes and/or sharp wave complexes; or periods of electrical suppression. Physiological parameters such as EEG variations due to ischemia are commonly said to be related to cumulative damage caused by the application of the retractor blade on the brain tissue. Analysis of the EEG wave form characteristics is essential in identifying and predicting future potential damage as it occurs and minimizing their effects before they become irreversible. Many patients may potentially demonstrate local EEG changes suggestive of ischemia or irritation in the course of a brain procedure.

In an embodiment, the present disclosure discloses a system that employs sensors using an automated onset detector to minimize the delay between the onset of electroencephalographic alterations and treatment. In an embodiment, the system includes a matrix array geometry of sensors. In an embodiment, the system alerts staff to the ischemic onset. In an embodiment, an alert activates a drug infusion pump. This can be accomplished, for example, via a computer, that can initiate a delivery of a pharmaceutical agent(s). In an embodiment, the system is equipped with a processor which analyzes the detected signals for indications of the onset of a physiological event. The physiological event can be, for example, an ischemia or irritation.

Variability of EEG among patients can limit the detection of physiological events to only the most common patterns and can contribute to a high false-alarm rate. However, the present disclosure describes a solution to this problem by providing a system that automatically adjusts to each patient. Thus, a physician is not required to configure the system prior to each use. In an embodiment, the system is fitted with a mechanism that allows an operator to manually adjust the settings of the system. In an embodiment, a display menu is provided to allow an operator to select the appropriate item to adjust the system. In an embodiment, the adjustments allow for better categorization of the area, and the corresponding wave form type of that region in the brain. This is a patient-specific method that exploits the consistency of ischemic vs. non-ischemic EEG within patients. A classifier determines to which of two classes an observation most likely belongs based on a comparison of its features with the learned features of training examples from each of the two classes. In an embodiment, the classifier includes threshold parameters. In an embodiment, the system captures the morphology of EEG waveforms by measuring their energy at different time-scales in a local setting. This is possible because the sensors described herein provide superior sensitivities and capabilities for discerning biopotentials. The system can be fitted with a multiple solution wavelet decomposition which encodes spatial distribution by the placement within the vector of features. The can be accomplished using, for example, a Zalink part number Z170101 and processed by the microcontroller, for example, a TI part number MSP430F1611.

Bioelectric signal measurements and the construction of cell and organ electromagnetic field activity maps based on these measurements has a wide range of biomedical application in modeling and diagnostic procedures of healthy and diseased living tissues. The difficulty in these measurements and mapping procedures mainly relates to the degree the measuring tools interfere with the measured bioelectric fields and signals, thus affecting the fidelity of the boundary conditions from which the modeling and diagnostic maps are generated.

The minimally invasive non-contacting biosensor technique described in the present disclosure advantageously applies high impedance and low capacitance semiconductor sensing technology combined with techniques of eliminating the traditional double-layer ionic transfer and conductive charge injection effects. The double-layer ionic transfer and conductive charge injection effects distort the regular electromagnetic fields and activation potentials of the measured tissue. The system can also be used to diagnose conditions of cardiac arrhythmias providing ECG signals for electrocardiographic mapping, and provide EEG signals for the localization and analysis of spontaneous brain activities for pre- or post-operational monitoring.

Non-contact measurements (NCM), described in the present disclosure is based on the ability of the apparatus to measure the bioelectric potentials. In an embodiment, the NCM is achieved by the use of an integrated mosfet array sensor system. In an embodiment, the system uses a non-invasive boundary condition sensor technique in which a plurality of measuring devices are embedded on a retractor blade. Te measuring devices collect simultaneous signal data sets from the surface of an area covered by the brain retractor adjacent to the patient's tissue. The usefulness of the collected data is two-fold: (i) the location of the data points and the measured signals (such as, for example, EEG, pressure and temperature), which provide direct and local values of critical parameters at particular places patient's tissue, such as the surface of the brain, and (ii) the data location and signal value-matrixes provide the boundary conditions of the patient's tissue so as to compute and map the field and signal propagation distribution within the volume of the tissue. In the situation where the brain is being monitored, this system advantageously pinpoints the main sources and high intensity loci's of spontaneous brain activity. From the specific data (i) the physician can monitor particular areas and symptoms, such as the onslaughts of an impending ischemia, for example, using data from the plurality of measuring devices and (ii) an EEG map can be generated (for example, using the Inverse Problem method) by which the condition of the ensuing ischemia state and pathology is used to predict that state of the local brain tissue under the retractor surface area and/or the proximal area of the operated region underneath the retractor blade.

The accuracy of the measurement for both the monitoring and mapping procedures depends on the non-invasive qualities of the measuring device. The interface of the present innovation with the brain tissue is capacitive. The dielectric between the device sense-plate and the brain tissue is an insulating material in the electrolyte of the cerebro-spinal fluid (CSF). The electrostatic field conditions need to be computed for this interface and for the Inverse Problem mapping method using Poisson's and Laplace's equations where the measured data serves as the boundary condition for all computations. The constants for dielectric coefficients of brain tissue, are for example: gray matter dielectric constant is about 56 Kappa, brain's white matter is about 43 Kappa, while brain's meninges is about 58 Kappa. Further details of the boundary condition modeling will improve the accuracy of the predictable algorithm when using the apparatus 900. Further specificity of the charge density coefficient of the cerebro-spinal fluid can be estimated or continuously measured for these computations.

The Poisson's Equation teaches that the electrostatic field in a material with dielectric and charge properties is:

$$\frac{\partial^2 V}{\partial x^2} + \frac{\partial^2 V}{\partial y^2} + \frac{\partial^2 V}{\partial z^2} = -\frac{\rho_v}{\varepsilon} \quad (1)$$

where $\rho_v$ is the measured volume charge density, and $\varepsilon$ is the average dielectric constant Known solutions of partial differential equations fitting the Poisson's Equation is performed to obtain the electrostatic field distribution along the surface area of the measurement site and/or the field map within the tissue.

Laplace's Equation describes for the charge-free insulation layer (reference designator 11) of the sensing array 400:

$$\frac{\partial^2 V}{\partial x^2} + \frac{\partial^2 V}{\partial y^2} + \frac{\partial^2 V}{\partial z^2} = 0 \quad (2)$$

The solution methods, using the boundary condition locations and measured signal values are similar to the Poisson's Equation. Other numerical solutions may employ a known differential equation solutions which results in a minimum error for the boundary conditions.

The non-contacting 803, sensing by the membrane 201, surface 17, has an insulated silver-plate to sense the facing tissue electrostatic field (Contact area 801). The electric field intensity between this plate and the tissue is calculated from the Poisson's Equation also which is simplified for the case of two parallel plates representing the capacitor formed by the insulated sensing plate 17, and the tissue 800, at distance d.

$$E_d = \frac{\rho_v \cdot d^3}{3 \cdot \varepsilon} - \frac{\rho_v \cdot d^2 \cdot d_0}{2 \cdot \varepsilon} + \frac{\rho_v \cdot d_0^3}{12 \cdot \varepsilon} [V/m] d \geq d_0 \quad (3)$$

where $d_0$ is the minimum distance defined by the insulation layer.

However, using any of these methods requires accurate boundary condition measurements which produce minimum error due to the measurement itself. The present disclosure describes measuring techniques which enable such measurements.

In an embodiment, the present disclosure describes a surgical retractor having an integral sensor in the blade to detect and monitor the pressure as well as local EEG signal of the tissue underlying the retractor blade. In an embodiment, a surgical retractor is described which has a sensor embedded therein to directly monitor impedance variation in the underlying tissue. In an embodiment, a retractor is described which has a removable sensor in the blade configured to monitor the tissue etiological state as a function of its electrical conductivity.

In an embodiment, a surgical retractor having a matrix sensor array embedded therein is described which directly measures the local EEG fractionated and continuous signals, analyzes such bioelectrical potentials and displays a measurement.

In an embodiment, a surgical retractor is described having a matrix array formation so as to directly measure the local EEG fractionated and continuous signals, analyze such bioelectrical potential and display such.

In an embodiment, a surgical retractor with an analyzing module for processing EEG signals so as to render a predictive value relative to the viability of the local tissue sampled by the apparatus is disclosed.

In an embodiment a monitoring system for displaying measured parameters such as EEG, Pressure, Temperature, and Impedance of the tissue underlying the surgical retractor is disclosed. The sensor embedded in the blade can take the form of any of several sensing devices which directly measures a parameter indicative of cellular metabolism, tissue blood flow, or tissue oxygenation as it is reflected by its electrical equivalent values through capacitive, conductive, and or resistive processes.

In an embodiment, a process is described which allows a surgeon to accurately control and minimize the disturbance of the brain tissue during surgery, thus minimizing the potential for permanent damage. This is achieved by the use of an alert signal or announcement on the display or with the aide of audio signals reflective of the state(s) of the apparatus and the tissue in question. In an embodiment, a removable detector positioned on a surface of the retractor blade is provided. In an embodiment, the detector can be selected for the specific tissue in the surgical area. In an embodiment where the detector is be coupled to a blade, the blade, and thus the detector, may be changed according to the requirements of a particular surgical procedure. In an embodiment, different detector can be coupled with different blades according to the desired procedure and tissue cite.

In an embodiment, the detector can measure one or more electrophysiological parameters, such as, for example, brain compliance or elastance, EEG, cerebral impedance, partial pressure, temperature, or a combination thereof.

In an embodiment, a plurality of sensors is strategically mounted in a matrix like arrangement so as to monitor various parameters, such as, for example, surface tension, blood flow, tissue metabolism, EEG, or the like. In an embodiment, EEG and pressure are combined so as to enable a predictive algorithm for the purpose of reducing brain injury due to ischemia.

In an embodiment, a surgical retractor includes an embedded inset in the retractor blade which includes a detector. The detector is in electrical communications with a signal processing unit and a remote display unit. Communications can be performed through wired or wireless communications including any appropriate protocol, such as, for example, serial, bluetooth, 802.11 a, b, g, n, or the like.

In an embodiment, the signal processing unit can be a multi-channel processor with a matrix array sensor. The signal processor is configured to convert the signals from the sensors from an analog signal to a digital signal using an ADC, digitizer, serializer and/or a buffer.

In an embodiment, the signal is amplified and fed to a display unit which may be a strip chart recorder, CRT or LCD display, or converted to an audio tone output.

In an embodiment, an audio alarm tone generator can be used for surgical procedures where the physician can be informed of the data resulted from the sensory outputs of the invention.

In an embodiment, the protocol of the audio pitch and the duration of tone pulses can be used to indicate the status of the underlying tissue conditions based on a "look-up tables".

In an embodiment, the alarm threshold can be defined as a measure of clinically relevant values as defined by the underlying conditions of the tissue examined so as to produce a tone or other output relative to the sensed variable which deviates from a permissible window and established threshold values.

Other objects, features and advantages of the present invention will become apparent from a reading of the following detailed description and appended claims when taken in conjunction with the accompanying drawing.

BRIEF DESCRIPTION OF THE DRAWINGS

FIG. 4A is an orthographic depiction of the various soft and siliconized spatulas employed as brain retractors for separating brain tissues.

FIG. 4B is an orthographic depiction of the Apparatus with an optional architecture of the Brain Retraction System indicating the connection to the host computer with an optical data link.

FIG. 6A is a detail view of a flexible circuit connector for a sensor array according to an embodiment.

DETAILED DESCRIPTION

Figure 1:
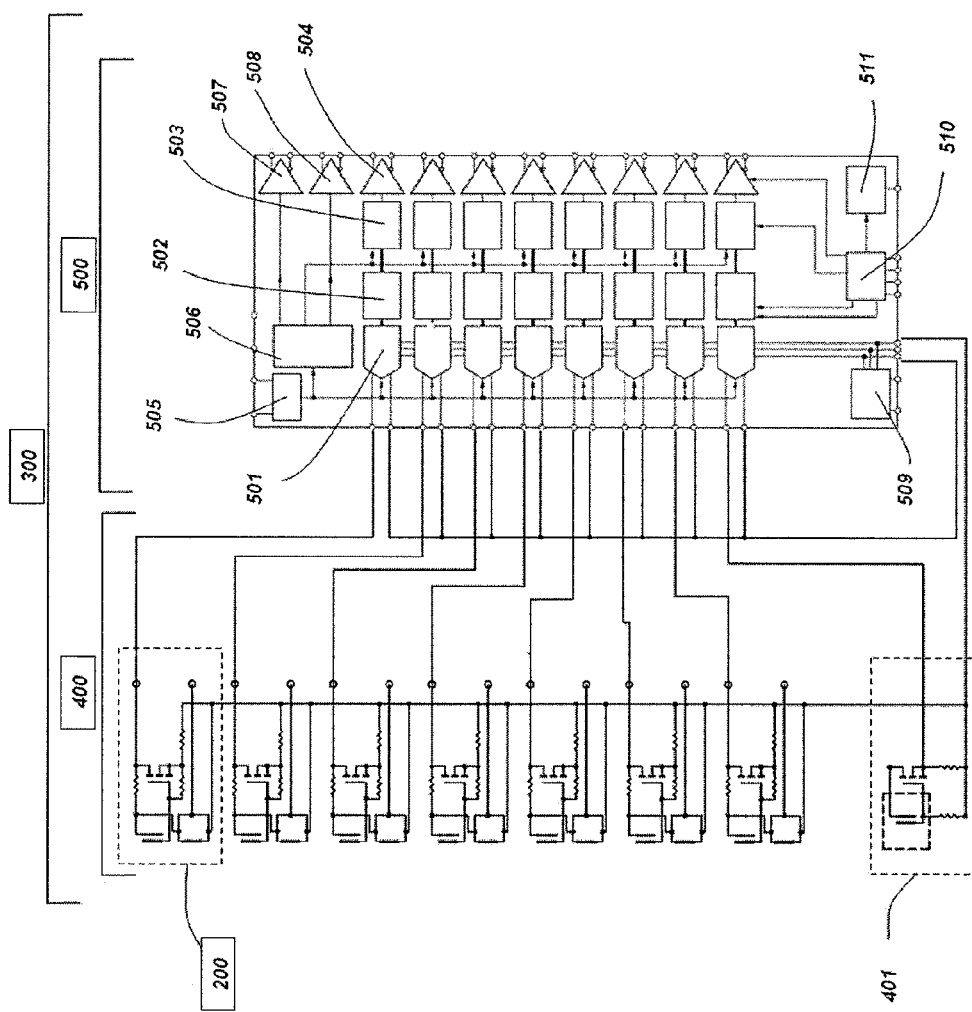
FIG. 1 is a schematic outline of an embodiment depicting the functional blocks of the system architecture.

FIG. 1 is a schematic outline of an embodiment depicting three blocks of the system architecture. One of the blocks is a multi channel integrated MOSFET sensor array 400. Array 400 includes modules 200. Modules 200 include pressure transducer 201 (shown in FIG. 1B) with its extended MOSFET gate 204, EEG detector-MOSFET gate, and temperature sensor 208. The circuit of the combined three sensors and its configuration are identified by reference designator 200. The sensor array 400, is linked to a calibration element 401. The calibration element 401 has another MOSFET with a fixed at a nominal potential. The difference between the MOSFET 204 and the reference element 401 provides the output. The integrated sensor array outputs are fed to the second block 500 of the system. The second block 500 includes an Analog to Digital Converter (ADC) 501, a Digitizer 502, a Serializer 503, an Output Driver 504, a Clock Buffer 505, a Phase Lock Loop 506, a clock Buffer #1 and #2 507, 508 respectively, a Reference 509, Set Registers 510, and ADC controls 511. In summary the integrated sensor array 400 is connected to an ADC with serial output 500 which forms an embodiment.

Figure 1A:
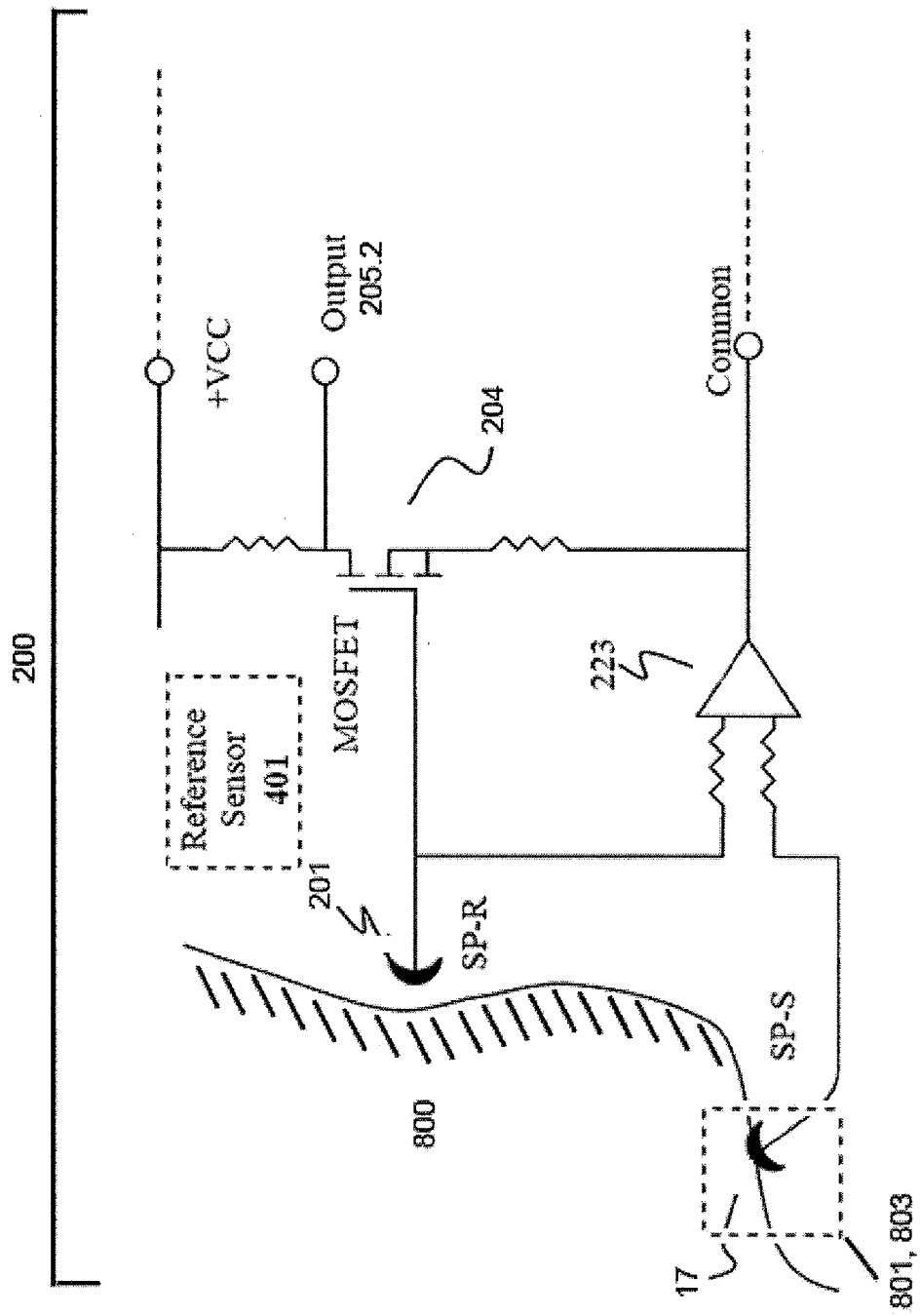
FIG. 1A is a schematic diagram of an embodiment of a MOSFET sensing stage.
Figure 1B:
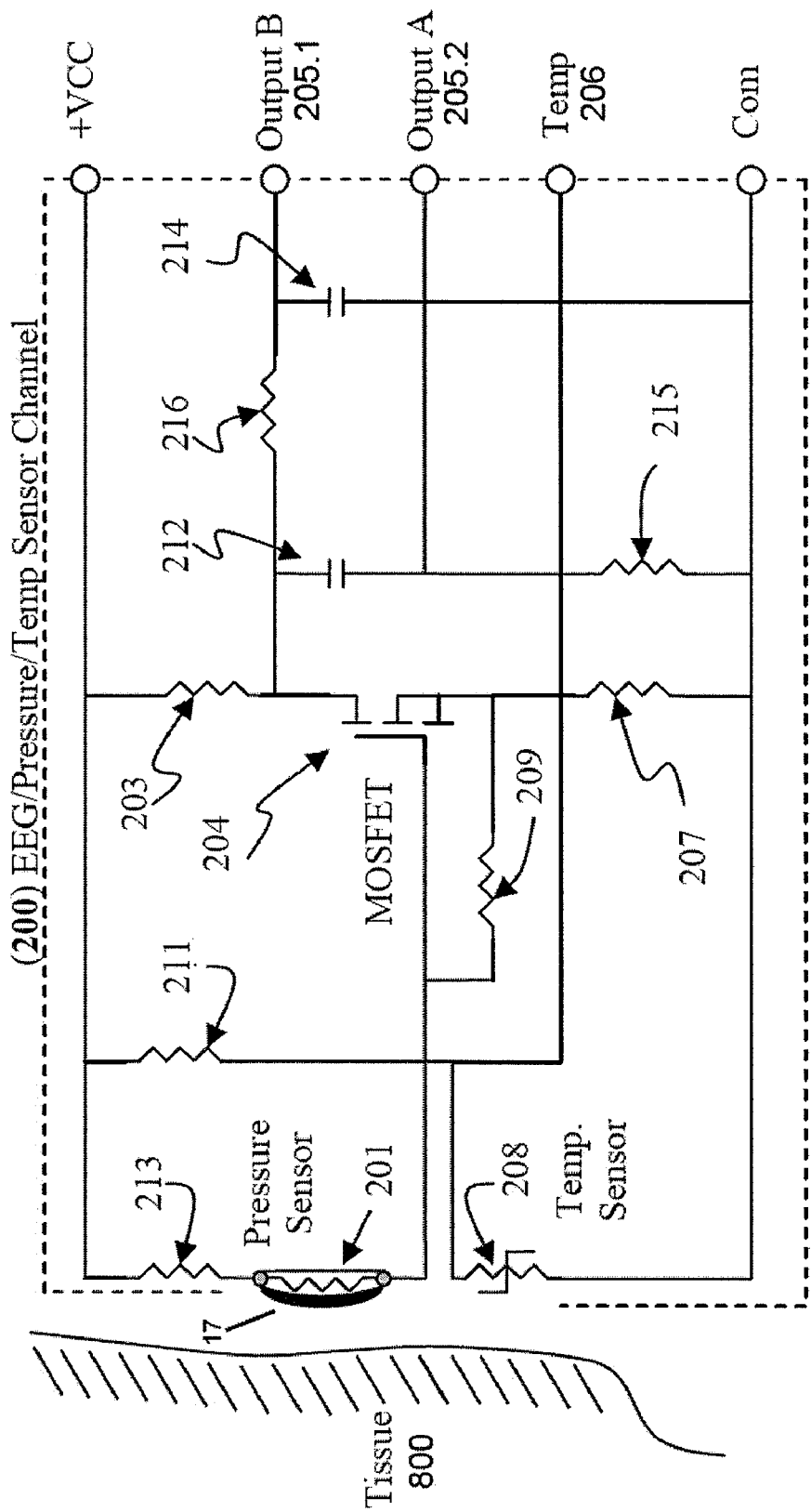
FIG. 1B is an schematic diagram of a single channel of a matrix array forming outputs for physiological measurements.
Figure 1C:
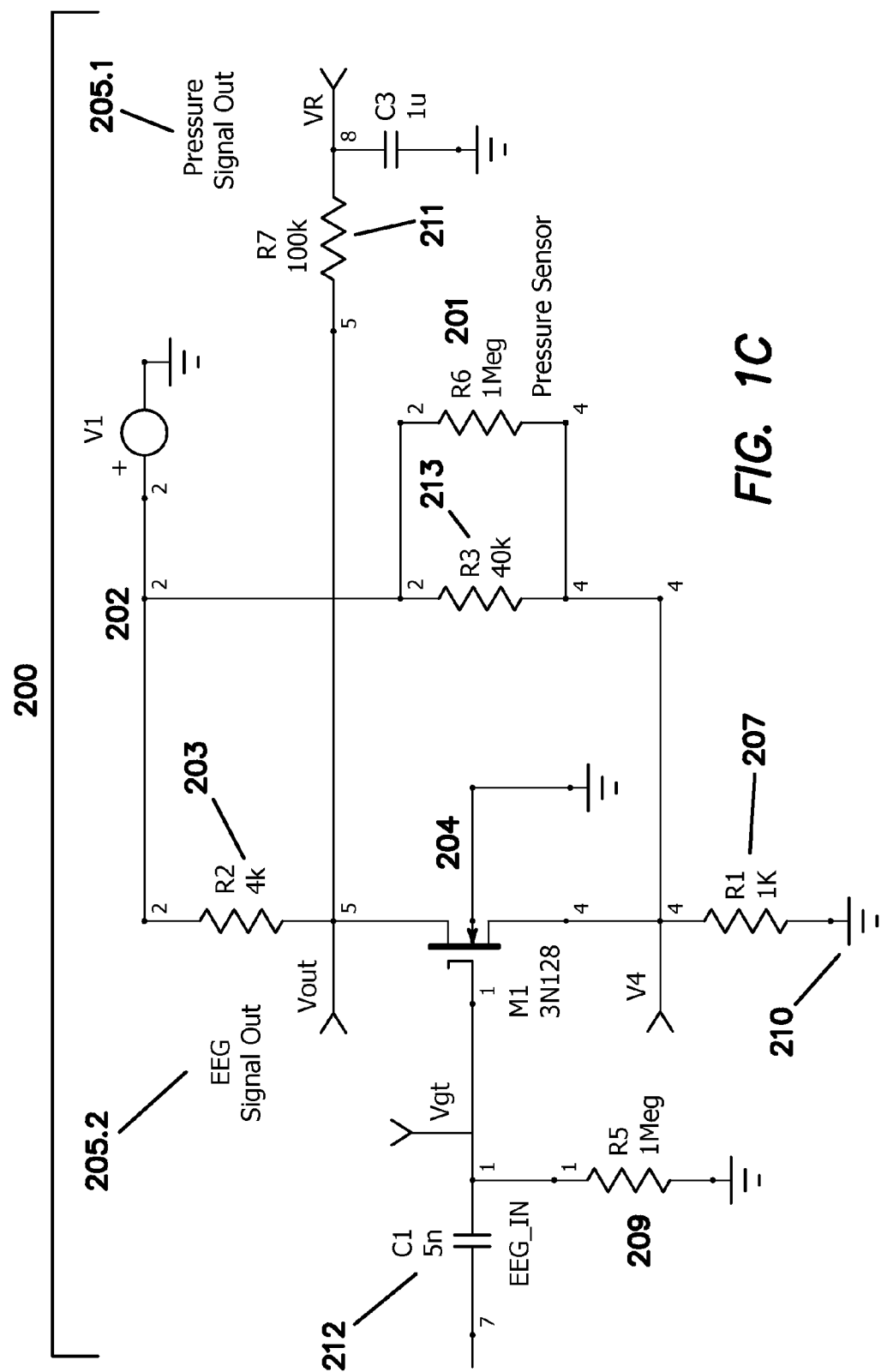
FIG. 1C is a graphic representation of a circuit layout with an integrated MOSFET sensor according to an embodiment.

The theory of operation and the functional relationship of the sensor and its operative characteristics is further defined and described by the ensuing FIGS. 1B and 1C their accompanying description. The architecture of FIG. 1 enables the detection of bio-potential signals and the pressure exerted on local tissue, as well as the temperature of the site in question.

FIG. 1A illustrates an embodiment of an integrated MOSFET sensor platform 200, including an EEG detection module with output 205.2, pressure transducer 201 (also shown in more detail in FIG. 1B) with sensing plate 17 (output designated as 205.1 in FIG. 1B) and Temperature sensor 208 (shown in FIG. 1B). The integrated sensory elements are designated as system 300 (shown in more detail FIG. 6). The system consists of 8 channels of sensing circuits 400 (shown in more detail FIG. 6), located along the flexible circuit board 10 (shown in FIG. 6). The basic electrostatic field sensing is performed by a depletion mode Field-Effect-Transistor MOSFET 204 in each channel. The sensor plate 17, facing the brain tissue 800, for each MOSFET is connected to the high impedance gate of the MOSFET which amplifies, the potential variations of the tissue sensed through the insulating gap between the tissue and the plate. The potential variations being the contact surface area between the sensor plate 17 and the tissue 800. One of the channels is used as the Reference Sensor 401. The average potential of the sensor plate 17 at this location is regulated to be close to zero in reference to a proximally placed single connection to the measured tissue 801. The voltage difference between the reference plate and the single tissue connection is measured by a high input impedance differential amplifier 223, the output of which sets the common potential for all cannels. The high impedance differential inputs to amplifier 223 reduces any conductive current below about $<10^{-9}$ Amps. As a result, charge transfer is minimized. The regulated Common, the auxiliary power connection (+VCC) and the Reference 401 voltages are floating with the potential of sensor plate 17, all of which is now practically at zero potential relative to the facing the tissue 800. The potential difference between the reference plate 17 and the regulated Common is representative of the double-layer potentials and the tissue impedances between 17 and 201. Once regulated by differential amplifier 223 and under steady state conditions, there are no charge currents flowing between these sensing points due to the measuring procedure itself. However, during maintained monitoring, periodic variations due to blood pressure or muscle contractions modulate the Common potential at the output of amplifier 223. The associated periodic charge variations average to zero. However, the absolute values of the slope-variations (derivatives) of the instantaneous Common potential are mainly the function of the impedance variation between 17 and 201 sensing spots. Thus, an average can be extracted and used as the impedance reference for the other sensing channels. Relative impedance variation is then computed from the ratio of sum of the average Output B 205.1 voltages (shown in FIG. 1B) divided by the reference Output 205.2 voltage of FIG. 1A and multiplied by the Impedance coefficient computed from the slope average:

$$Z_{rel} = K_{ref} \cdot \frac{\sum_{Ch-1}^{Ch-7} \int V_{O\_205.1}}{7 \cdot V_{O\_205.2}} \quad (4)$$

FIG. 1B. Is a schematic diagram (Single Channel) 200, of the MOSFET Sensing Stage which is one element of the matrix array 400 of sensors measuring the effective area of the sensor sheath 1 (shown in FIG. 5). The assembly 300 (shown in FIG. 6), is inserted as a flexible glove over the retractor blade 6 (shown in FIG. 5), or any of the possible spatulas such as 22, 23 or 24 (shown in FIG. 4). In an embodiment, the measuring instrument for sensing pressure as well as EEG bioelectric potentials are integrated using the sensing leg of the pressure sensor 201 with its insulated membrane 17, as C1 capacitor 212, of the MOSFET die 13. The integration of Pressure sensor 201, and EEG data via MOSFET 204, with description of the signal flow and a schema of the circuit is further described by reviewing the signals and the respective analysis noted in FIGS. 1C and 1D. A signal flow of the EEG IN sensing plate, C1 charges as a capacitor to a potential referenced to a tissue 800 anchor point common to all sensing channels. C1 sensing plate is insulated from the tissue by a thin layer of insulation material. This material could be any number of insulating materials, such as Capton, or Teflon, or any polymeric combination of these or similar materials. The capacitor plate absorbs the static and dynamic electrical charges from the adjacent surrounding tissue's 800 electromagnetic activity designated as area 801. The isolated MOSFET 204 element coupled with its pressure sensor 201, is detailed by the Figure with its associated circuitry comprising of R1 207, R2 203, R3 213, R5 209, M1 204, R6 201, C3 214, R7 211, and C1 212. Item 205.1 and 205.2 are designated as the outputs of signals generated as results of displacement of the diaphragm 17 for the pressure measurements and it is titled "Output B" and EEG signal is designated as "Output A".

FIG. 1B is a typical EEG signal at membrane 17 (EEG IN) is further clarified by observing the isolated MOSFET circuit M1 204 biases the input signal obtained through capacitor C1 212, and normalizes it to a output average signal level at VOUT such that the differentially measured signal output displays the AC and pulse components of the external EEG signal. The bipotential signals occurs between the two isolated MOSFET junctions designated by module 200, and potential difference (Voltage) due to cell membranes permeability to $K^+$, $Cl^-$, $Na^+$, results in variation of cellular potential with time, and it is the action potential, measured by the module 200, and the array of sensors designated as multi channel sensors 400. The electrodes in the prior art are typically made of metal-electrolyte interface. The interface impedance in this relation is represented as a capacitor, and in a non polarized electrode, the impedance is represented as a resistor. But in practice both capacitive and resistive components are present in the existing art, while the new method and the accompanying apparatus to this invention employ the MOSFET isolated junction, which measure the action potentials without the parasitic capacitive or resistive loads noted by the prior art.

FIG. 1C is a schematic diagram (Single Channel) 200 of an embodiment of the MOSFET Sensing Stage which is one element of a matrix array 400, with the circuit has components R1 201, V1 202, R2 203, M 204, VR 205.1, and Output Temp. 206, R1 207, Termistor 208, R5 209, R10 GRD, R7 211, C1 212, R3 213, and C3 214.

Figure 1D:
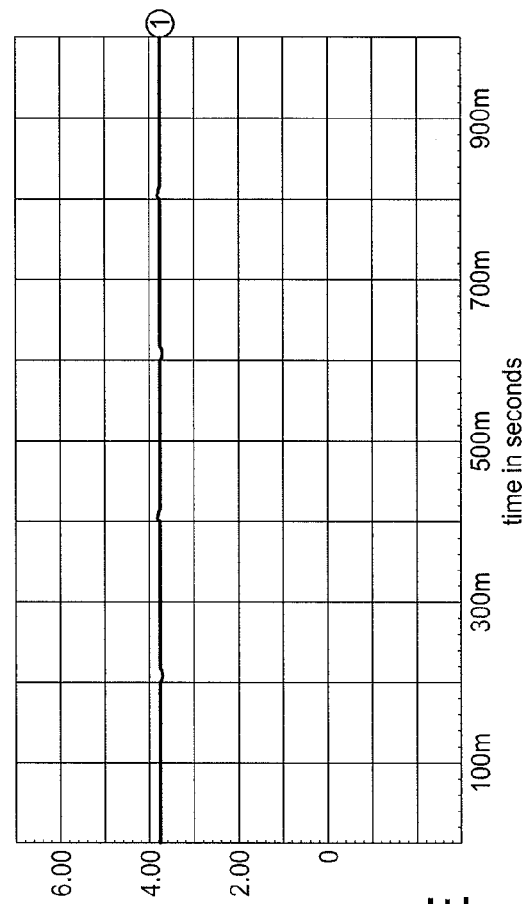
FIG. 1D is a graphic representation of a pressure signal level (VR).

FIG. 1D is a graph which depicts the EEG signal as a function of amplitude vs. time. The output from the biopotential at the tissue contacts between membrane 17, and the MOSFET 204 is received by output channel B 205.2. Each Channel 200, has three outputs. Output B and Output A are the EEG 205.2, and Pressure signals 205.1, respectively. The third output is the temperature measurement signal. These outputs are analogue signals. Each of these signals is converted into 16 bit data packets of digitalized information 500, which then are serially transmitted to the Microcontroller 603. Of course, a person of skill in the art would understand from the disclosure herein that any number of bits could be used for the data packets depending on the system architecture. The Microcontroller coordinates the signal processing and display procedures. A computer consol 605, with associated display 600, keyboard 606 and mouse 607 facilitates monitoring and mapping procedures. The host computer 605, is further fitted with analytical data processing so as to render the signals to form the links to the alert system. The alert System can be in the form of audio as well as visual display.

Figure 1E:
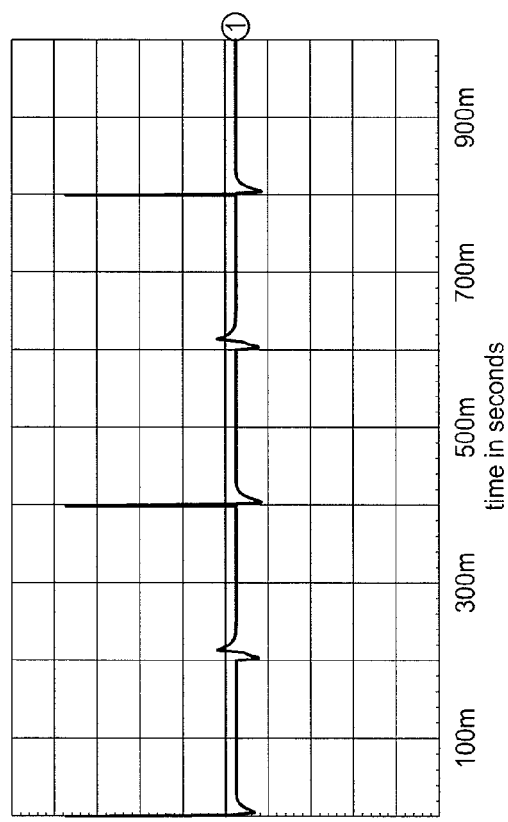
FIG. 1E is a graphic representation of an EEG signal level output.

FIG. 1E is a graph which represents the DC level following the pressure level changes of the Pressure transducer 201. The membrane 17 which forms the outer layer of the transducer acts as a surface and any displacement of 17 varies the resistance at the output channel 205.1. This signal is extracted by putting the MOSFET output signal through a low pass filter consisting of resistor 216 and capacitor 214. Such pressure level signal at Output A is shown in FIG. 1B.

Figure 2:
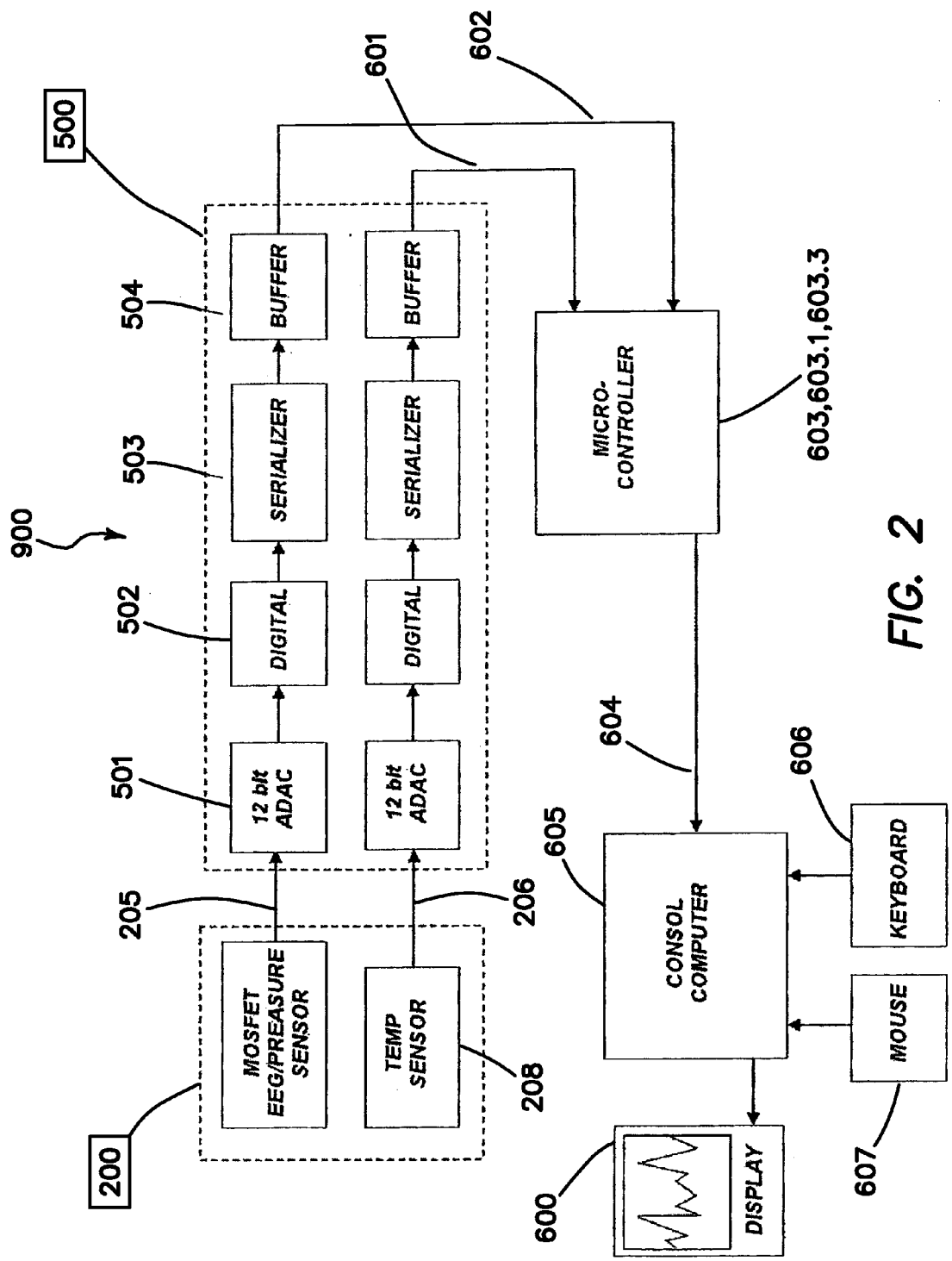
FIG. 2 is top level architecture depicting a channel of a sensor array as it is interconnected to the control and display system in an embodiment.

FIG. 2 is an illustration of the system 900, block diagram of the triple signal processing modules. Each Channel 200 has three outputs. Output A 205.1 and Output B 205.2 are the EEG and pressure signals respectively. The third output 206 is the temperature measurement signal. These outputs are analogue signals. Each of these signals is converted into 16 bit data packets of digitalized information 500, which then are serially transmitted to the Microcontroller 603. The Microcontroller coordinates the signal processing and display procedures. A computer consol 605 with associated display 600, keyboard 606 and mouse 607 facilitates the monitoring and mapping procedures, as well as the alert system notification via the algorithm as well as parametric analysis. The signal analysis relay on the fidelity of the signal generated by the apparatus 900, and interprets the signal as to its "Hjorth Parameters" such as Activity, Mobility and Complexity. Further analyses generated by the microcontroller 603. Or the host computer 605, is for example Amplitude, Mean Frequency and or Spectral density using an FFT method.

Figure 3:
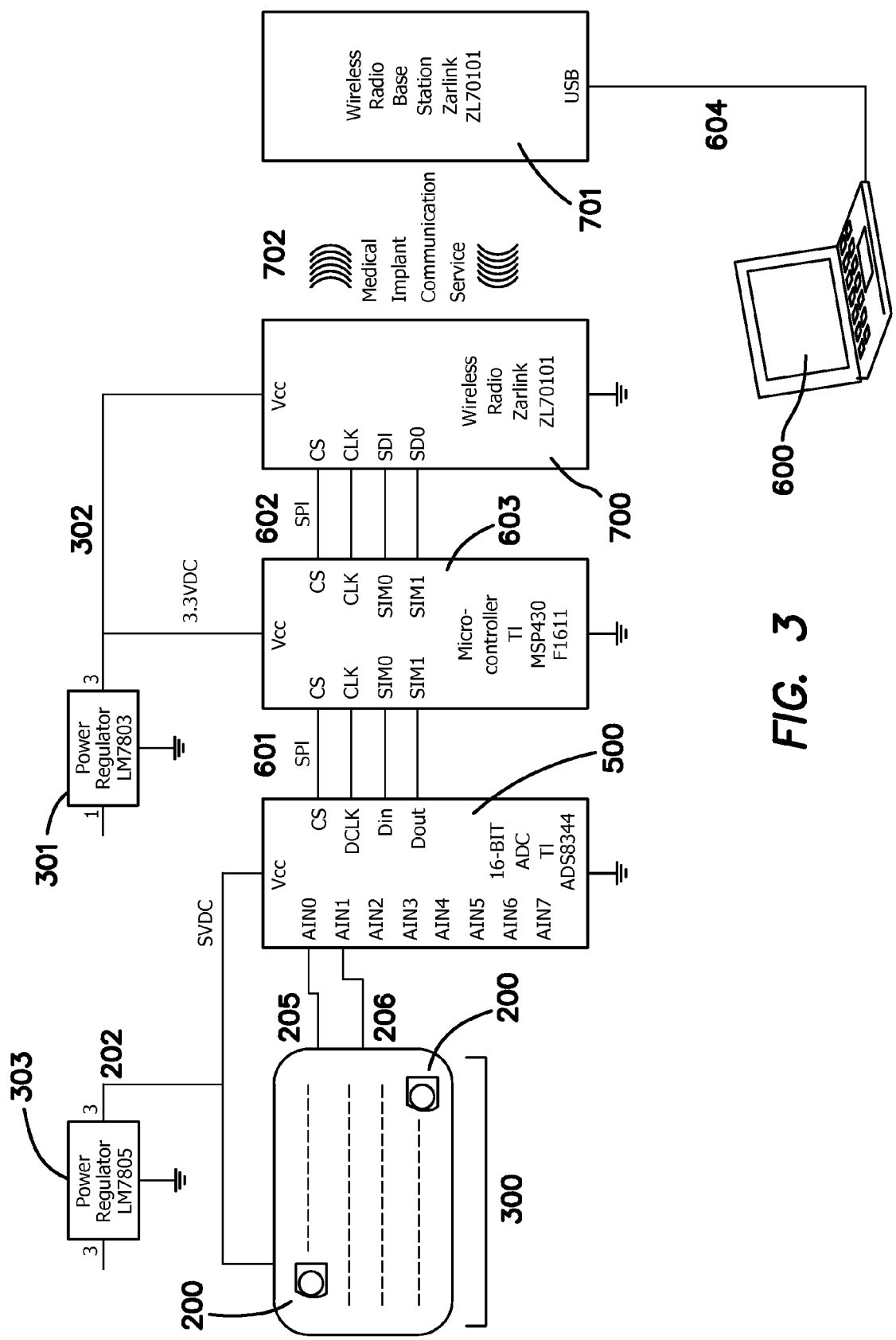
FIG. 3 is an embodiment of a lower level architecture depicting the elements which form a circuit.

FIG. 3 is an illustration of an embodiment of a brain retractor apparatus for measuring and predicting electrophysiological parameters employing an integrated MOSFET sensor array. In an embodiment, the integrated brain wave pressure sensor 200 produces analog voltage signals corresponding to EEG, pressure, and temperature information from the b rain surgical extractor system 300. The EEG signal (for example, as depicted in FIGS. 1D and 1E) is conveyed by the AC voltage at one of the outputs 205.2 of the brain wave pressure sensor while the DC voltage of the output 205.1 indicates the pressure sensed by the displacement of the transducer 201, via membrane 17. The other output 206, produces analog voltage corresponding to the temperature devise 14. These outputs (205.1, 205.2 and 206) are connected to an analog to digital converter 500, which digitizes the EEG, pressure, and temperature information at 16-bit resolution and produces the output in high speed serial data format. The ADC 500, such as LM7805 is connected to a microcontroller such as MSP430F1611 unit 603, over the Serial Peripheral Interface (SPI) Bus 601. The microcontroller is used for digital signal processing tasks such as filtering out the electrical noise on the signals and detecting alarms associated with device usage. The output of the microcontroller is then connected to a low-power wireless radio 700 over another SPI Bus 602.

The wireless radio, such as, for example, Zarlink Radio part number ZL70101, communicates over the Medical Implant Communication Service (MICS) wireless channel 702, to a wireless base station 701. The EEG, pressure, and temperature information as well as the alarm signals generated by the microcontroller are received at the wireless base station, which is connected to a computer 600 using a Universal Serial Bus USB 701. The computer displays the data and provides the feedback to the surgeon in real-time.

Figure 4:
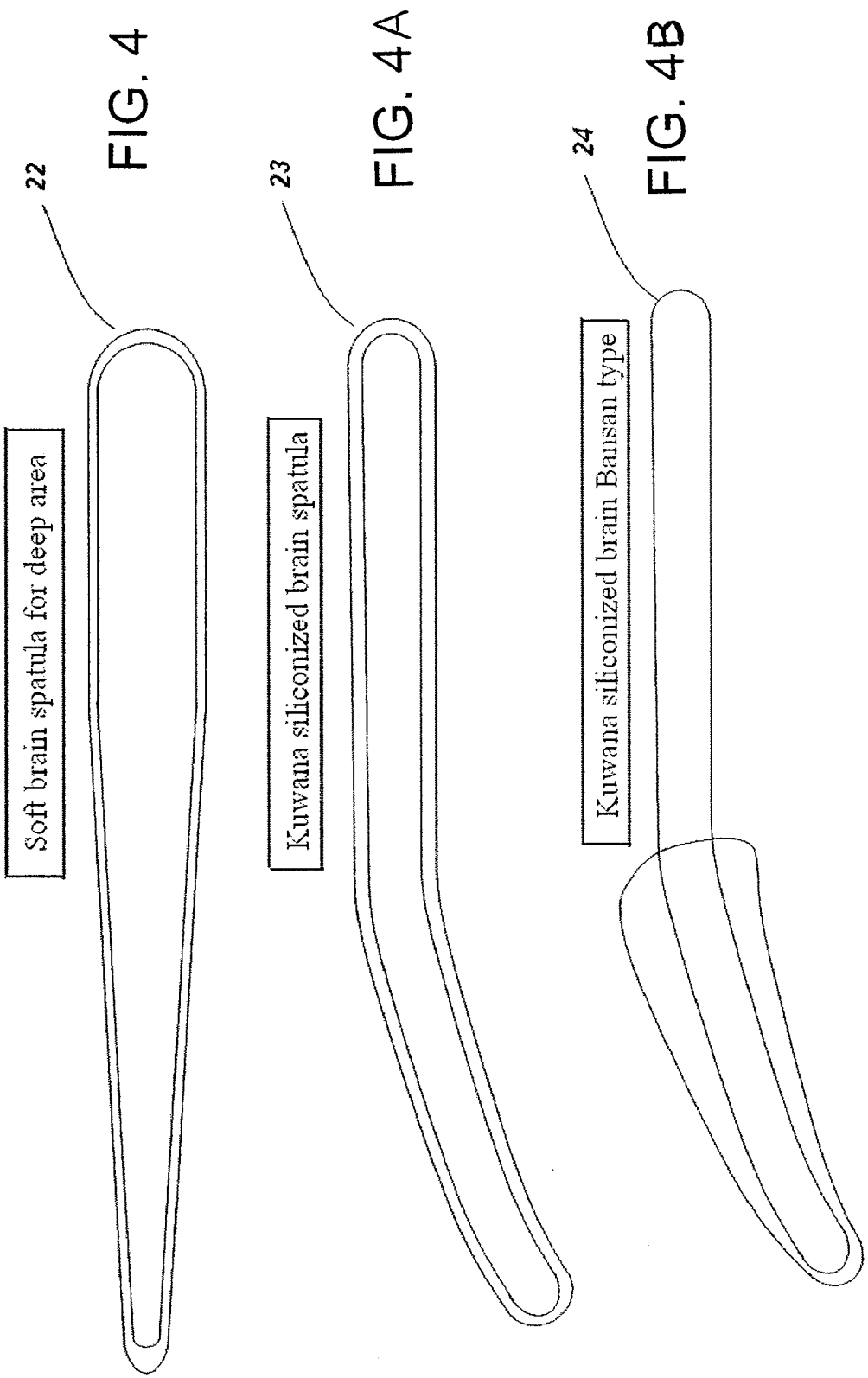
FIG. 4 is an isometric representation of the system formed out of sensor sheath, standard flexible retractor and amplifier/data acquisition box.

FIG. 4 illustrates several typical brain retractors such as soft brain spatula for deep area with 5 mm, 4 mm, and or a 2 mm tip designated by reference item 22, a Kuwana Siliconized brain spatula with 20×220 mm or 15×220 mm, or the use Kuwana Siliconized Bansan type brain spatula with dimensions of 18×30 mm, or 14×25 mm referenced by item 24. The foregoing are illustrated for example only and are not meant to be limiting. Those of skill in the art will understand from the present disclosure that other spatulas and brain retractors can be used with the teachings of the present disclosure.

Figure 5:
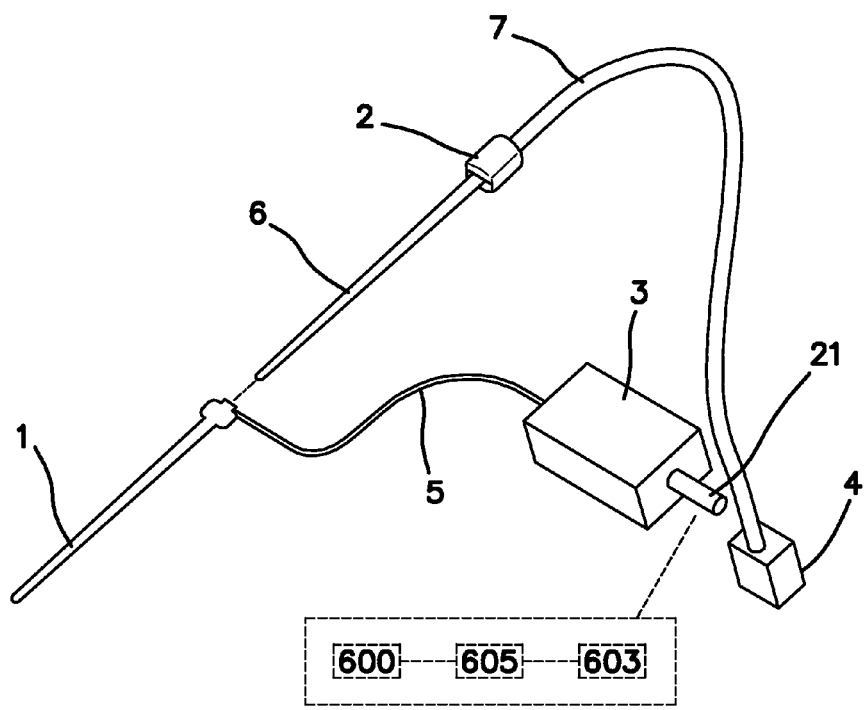
FIG. 5 is an illustration of the system shown in FIG. 2 further detailing the apparatus components with connections to the auxiliary elements by the use of a cable and the cable connector between the Integrated MOSFET sensor array and the retractor blade.

FIG. 5 is a representation of the system 900, further detailing the apparatus components with connections to the auxiliary elements 600,605, and 603 by the use of cable 21 (which can be a fiber optic data cable), and the cable connector 5, between the Integrated MOSFET sensor array 300, amplifier and data acquisition 3, and the retractor blade 6, mechanical assembly such as the Greenberg retractor 7.

Figure 5A:
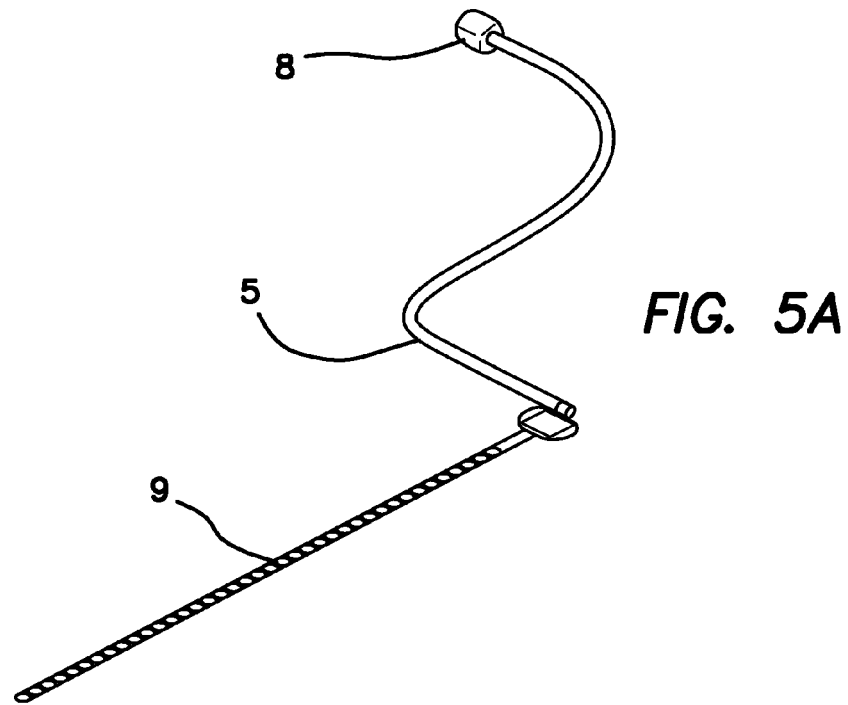
FIG. 5A is an isometric representation of a layout of the sensor geometry according to an embodiment.
Figure 5B:
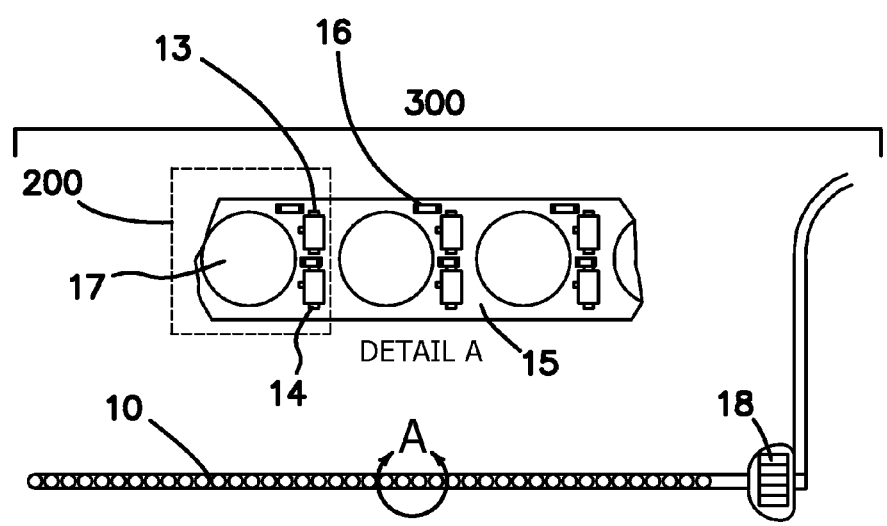
FIG. 5B is an orthographic representation of a sectional view of a pressure transducer with its associated electronics according to an embodiment.

FIGS. 5A and 5B are illustrations of the Sensor Array 9, with a layout configuration according to an embodiment. The pressure transducer 17, which also function as the surface area for detection of the EEG signals, includes a circular membrane. The constriction of the transducer 17, such as commercially available from Tekscan USA and branded as Flexi Force A201 is a force sensor with an ultra-thin, flexible printed circuit. The force sensors are constructed of two layers of substrate (polyester/polyimide) film. On each layer, a conductive material such as silver is applied, followed by a layer of pressure-sensitive ink. Adhesive is then used to laminate the two layers of substrate together to form the force sensor. The active sensing area is defined by the silver circle on top of the pressure-sensitive ink. Silver extends from the sensing area to the connectors at the other end of the sensor, forming the conductive leads. Transducer 17, in this embodiment, includes the ability to act as a force sensing resistor in an electrical circuit. When the force sensor is unloaded, its resistance is very high. When a force is applied to the sensor, this resistance decreases. The output of the transducer provides an indication of both the force vs resistance and force vs. conductance (1/R). The conductance curve of transducer 17 is linear, and therefore useful in calibration of the device via a command by the microcontroller 603. The circuit 200, includes a resistor 16, a MOSFET Die 13, and a temperature sensor 14. The configuration and geometry of the Sensor Array 9, with its functional counterpart 200, as it is described contains multiple units, and, for example, in an embodiment, at least eight elements forming a chain 400. The Sensor Array 9 covers the surface area of the retractor blade 6. The entire assembly is mounted on a flexible printed circuit 10, to form a matrix arrangement (detail A). The assembly 9, is further isolated electrically with insulated flexible substrate 15. FIG. 5A further describes an embodiment of the connection of the sensor array 9, to the pressure and EEG A/D 8 Channel IC 18. The sensor array 9, is connected to the processing unit 603, 605, and display unit 600, via cable 5, and connector 8.

Figure 6:
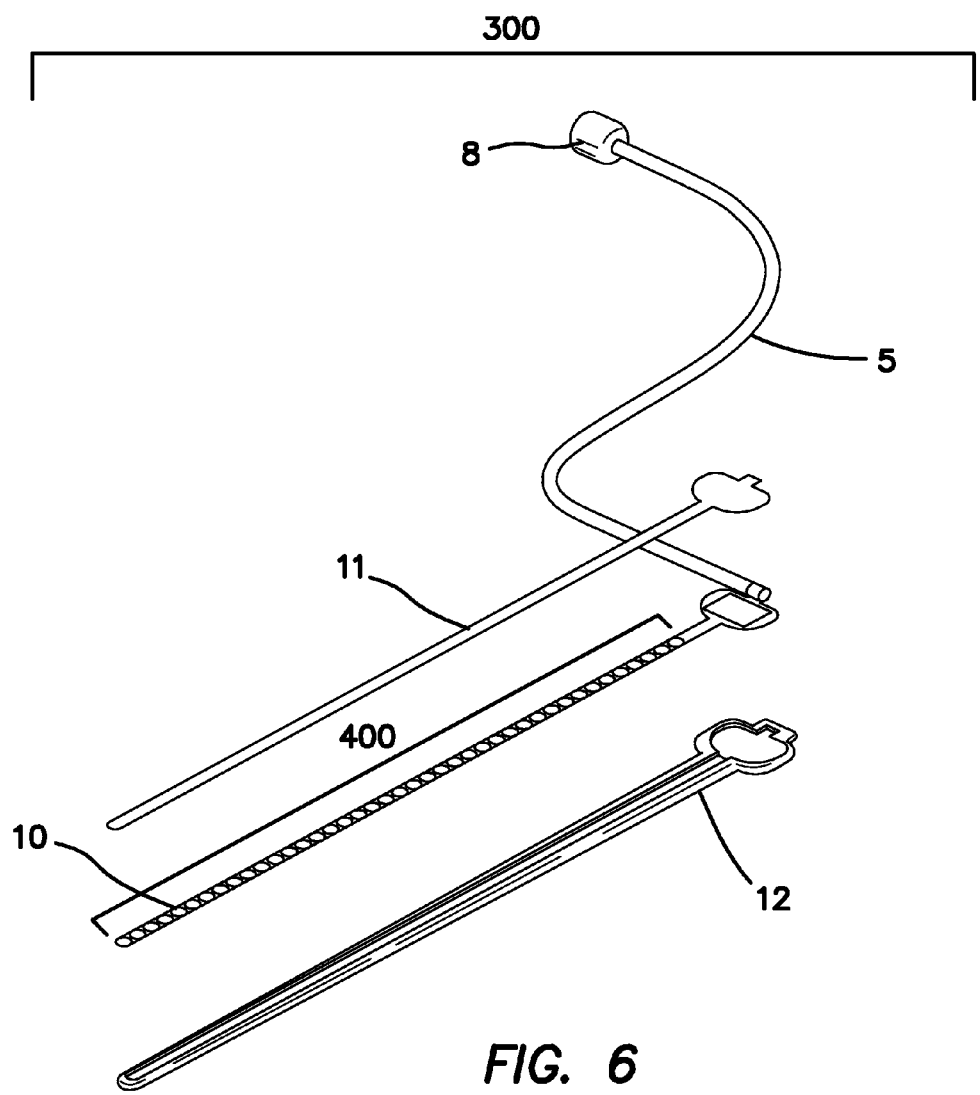
FIG. 6 is an isometric depiction of an embodiment with a sensor array protected by a disposable protective polymer, enabling the sterilizing and hermetic packaging of the device.

FIG. 6 is an isometric depiction of the apparatus 900, including sensor sheath 1, a disposable cover placed over the Integrated MOSFET sensor array 400, a standard flexible retractor blade 2, with a flexible arm such as Greenberg retraction assembly 7, and an amplifier/data acquisition box item designated as 3. The sensor sheath 1, is a disposable cover that is placed over the Integrated MOSFET sensor array and is formed out of material such as natural rubber latex (NRL). The cover 1 is a protective layer formed over the retractor blade 6, which form the sterilized surface of the sensors, further reducing the cost of the apparatus, so as to enable reusability of the Integrated MOSFET sensor array without the need to employ a high temperature autoclave sterilization, while using Ethylene oxide gas for the objects forming the Integrated MOSFET sensor array 300 and its sensitive elements to temperatures greater than 60° C. The sensitive elements can include, such as, for example, the plastics, optics and electrics.

FIG. 6A is an orthographic representation of the sensor connector assembly 8, depicting the cable 5, the temperature A/D 8 Channel IC 20, the isolated flexible substrate 15, and flexible printed wiring circuit 19. This layout further isolates electrically the apparatus 900, from the retractor blade 6, and the brain tissue 800.

Figure 7:
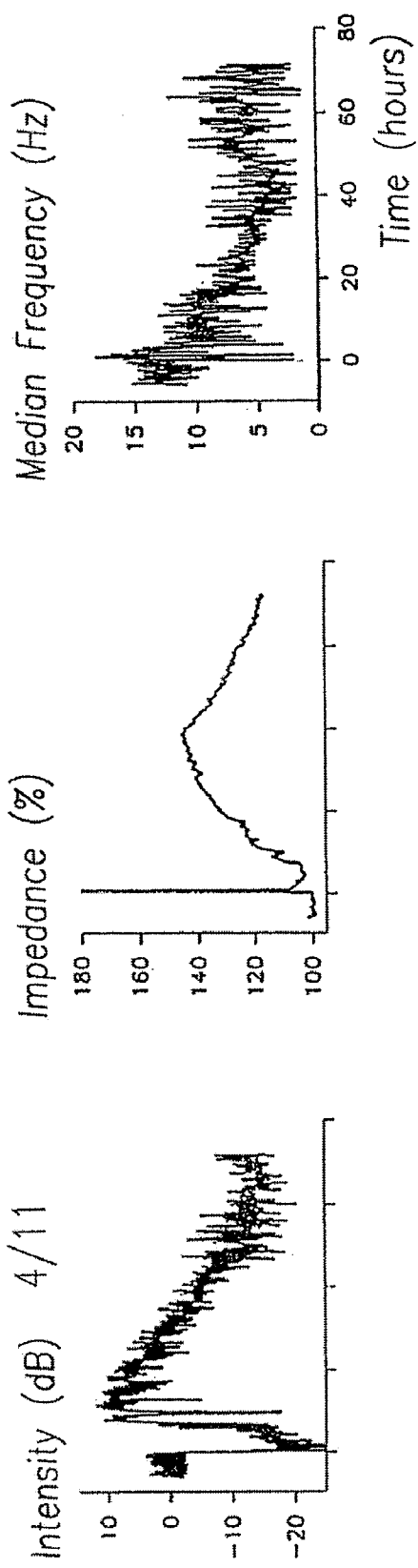
FIG. 7 is a graphic description of an EEG signal with a corresponding impedance graphs.

FIG. 7 is a graphic display of a typical long term EEG signal recording with the corresponding Impedance and Frequency-domain diagrams. The Impedance diagram is obtained from the measurement technique described in FIG. 1A. The EEG signal is dB and the Impedance display is in percentage for showing relative trends over time. The Impedance calculation derived from equation (4) above.

$$Z_{rel}\ \% = K_{ref} \cdot \frac{\sum_{Ch-1}^{Ch-7} \int V_{O\_205.1}}{7 \cdot V_{O\_205.2}} \cdot 100 \tag{5}$$

Figure 8:
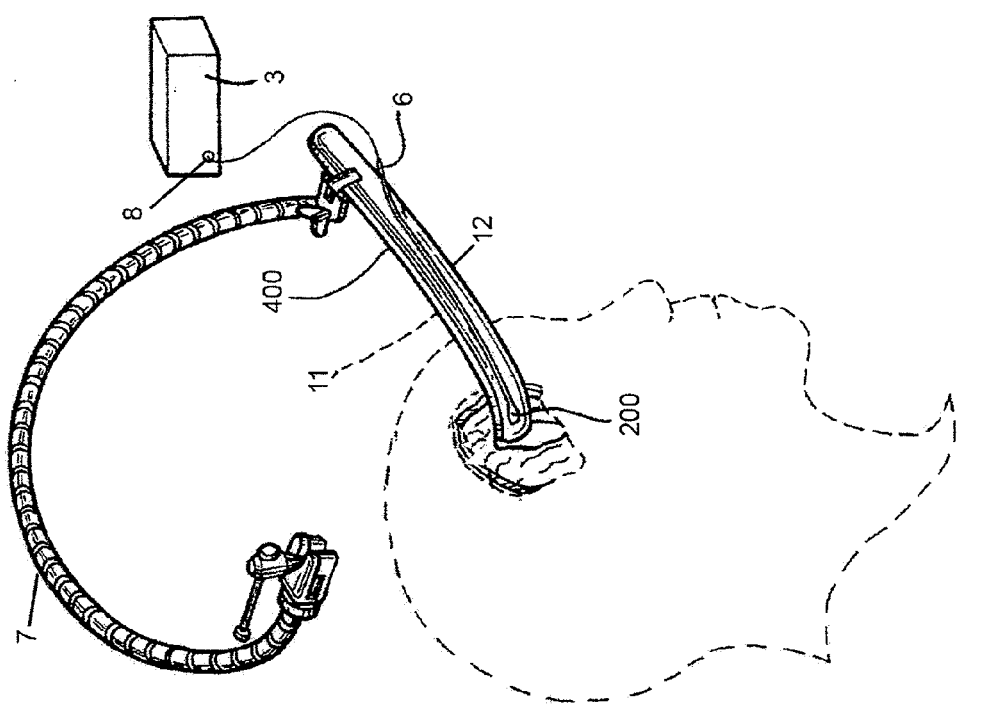
FIG. 8 is an illustration of a brain retractor blade attached to a "snake" retractor blade handle, which is hooked up to a Mayfield head holder.
Figure 8A:
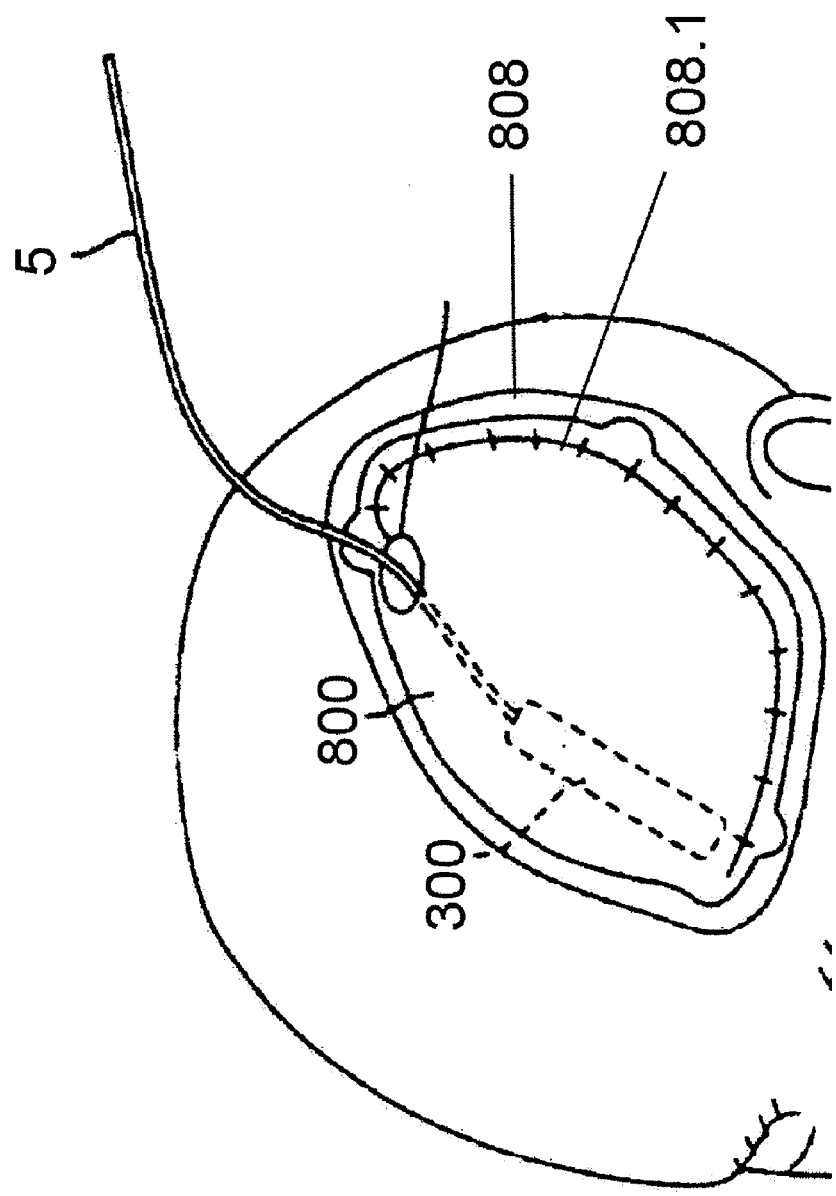
FIG. 8A is an illustration of a craniotomy using a retractor blade.
Figure 8B:
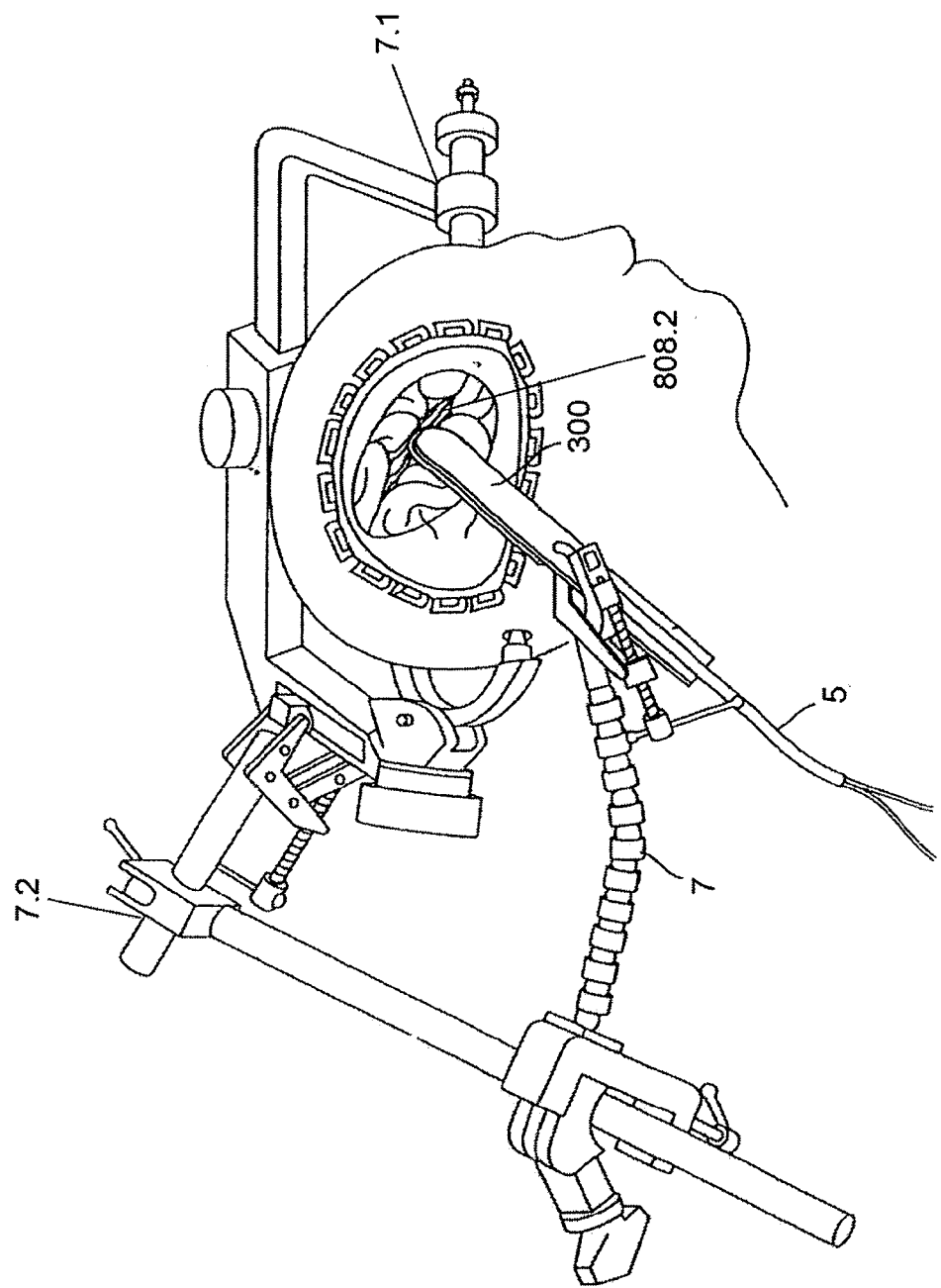
FIG. 8B is an illustration of a brain retraction apparatus in a setting with Greenberg retractor.

FIG. 8 is a schematic description of a retractor blade 6, with a MOSFET sensor array 200, attached to a "snake" 7, retractor holder. The patient is placed in Mayfield pins 7.1, for the craniotomy 808. The head is shaved and prepped. A craniotomy is performed overlying the lesion, and the bone flap is removed. The dural edge is tacked up to the underlying skull 808.1. The dura is then opened in a cruicate manner, exposing the brain.

The sylvian fissure is opened using microsurgical technique, and a retractor is placed in the frontal lobe 808.2. If a retractor is placed for the underlying temporal lobe 808.3, two retractors will be needed. Each retractor 300, is bent to the shape desired, and hooked up to a retractor "snake." 7, the snake is then attached to the Mayfield head holder 7.2. Underlying ischemia will be detected using the MOSFET sensor array 300, and transmitted (via corn. Link 604 to a PC station 605, monitor 600, alerting the surgeon (with the use of look-up-tables 603.1, so as to provides alarm notices 603.3 in real time.

Figure 9:
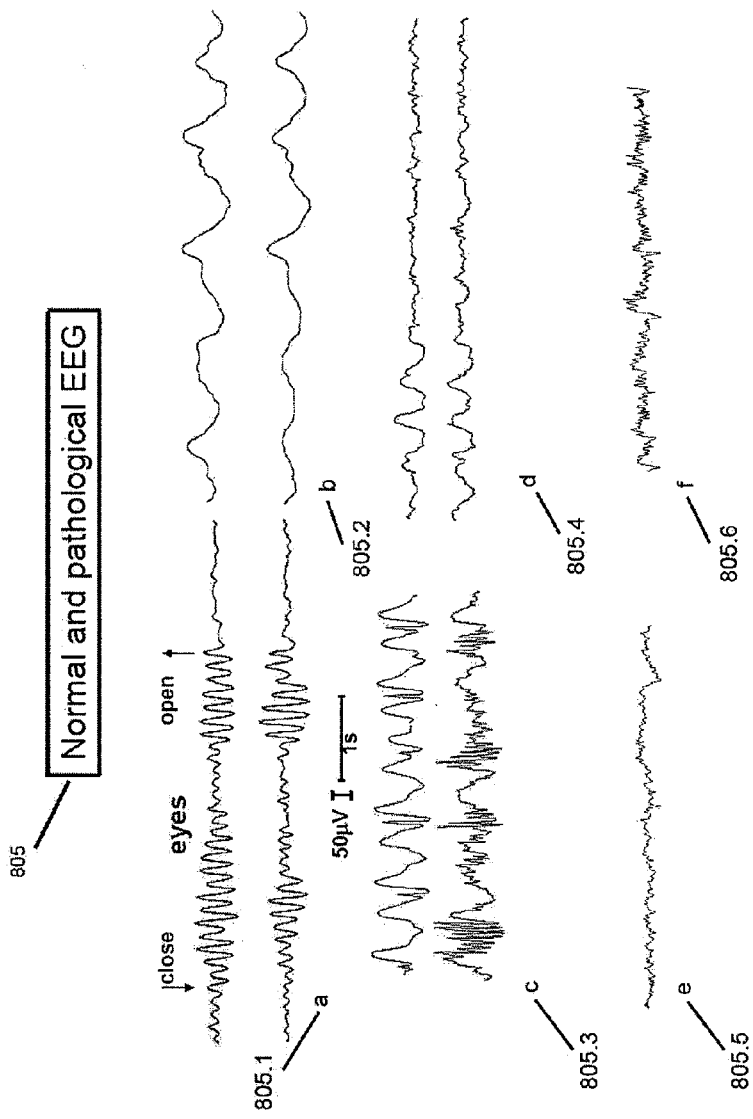
FIG. 9 is a depiction of various normal and pathological brain waves used in illustrating the ability of the apparatus to define alarm threshold parameters.

FIG. 9 is a depiction of various brain waves typical of rhythms, powers or amplitude corresponding to occurrences which the presently described is capable of identifying and isolating in an embodiment. Panel (a) 805.1 corresponds to normal (under no specific conditions) electroencephalogram brain wave reading. The leftmost signal corresponds to a typical beta band waves when the person has his eyes closed. The center wave corresponds to the change in rhythm when the eyes are open, and so forth. Panel b, 805.2 suggests a similar wave pattern of a person under a different task, stereotypically of 'default mode' activity that could arise in the temporal or frontal lobes under EEG readings. Panel c, 805.3 corresponds to the same subject as panel b, 805.2 while the person is having an epileptic seizure. The rhythms become more pronounced, with rapid ripples and increased synchronicity on the envelope of the prior wave bands. In an embodiment of the presently described system employing the brain retractor 300, the system enables the physician to discern and identify these changes in power. The system 900 alerts the physician (using AI routines 603.2) on the potential seizure occurrence 603.3. Panel d, 805.4 is suggestive of an unconscious person's EEG reading. The decreased power, yet stable rhythm, are suggestive of a loss of consciousness that can be alerted by use of the alert notices 603.3. Panel e, 805.5 indicates the EEG reading of a lesion brain region, suggestive of the immediate effect of permanent pressure on a tissue 800, reflected in the EEG reading and is identified ad-hoc by the system 900. Panel f, 805.6 graphically represents the effect of over-pressure such as indicated by Mean Arterial Pressure minus the Brain Retractor Pressure producing a state whereby the differential pressure is less than 70 mm Hg (MAP-BRP<70 mm Hg) so as to generate a typical wave reading as indicated. A patient undergoing pressure of 550 mm of water shows an increased wave amplitudes in the EEG reading, as well as short ripples suggestive of burst of evoked potential in the area of where the brain retractor is exerting its pressure. Qualitative indications of the relationship between the ethological and mechanical state of the cellular structure under pressure and its electrical EEG counterpart is indicated. As a reference we show below the continuous reading of the same area when no pressure is applied. Notice the similarity between over-pressured brain region under the retractor in panel f, 805.6 and the permanently lesion one in panel e, 805.5. All of these cases are identified and isolated by the presently described system further producing the necessary alerts 603.3 in a form of visuals or audio notices so as to enable the reduction of brain retraction injuries.

Although the foregoing invention has been described in terms of certain preferred embodiments, other embodiments will be apparent to those of ordinary skill in the art from the disclosure herein. Other combinations, omissions, substitutions and modifications will be apparent to the skilled artisan in view of the disclosure herein. It is contemplated that various aspects and features of the invention described can be practiced separately, combined together, or substituted for one another, and that a variety of combination and subcombinations of the features and aspects can be made and still fall within the scope of the invention. Furthermore, the systems described above need not include all of the modules and functions described in the preferred embodiments. Accordingly, the present invention is not intended to be limited by the recitation of the preferred embodiments, but is to be defined by reference to the appended claims.

What is claimed is:

1. A brain retractor having a plurality of non-contact EEG sensors configured to measure EEG signals and the pressure exerted on a brain during surgical procedures of the brain, the brain retractor comprising:
   a brain surgery retractor blade;
   a plurality of non-contact EEG sensors disposed on said retractor blade, each non-contact EEG sensor configured to provide an indication of electrical signals associated with the patient's brain;
   a plurality of pressure sensors disposed on said retractor blade;
   a temperature sensor disposed on said retractor blade;
   a processor in communication with said non-contact EEG sensors to determine an indication of the EEG of the brain; and
   a display in communication with the processor, the display configured to receive information from the processor and provide an indication of the EEG, and
   wherein the non-contact EEG sensors are disposed within the pressure sensors.

2. The brain retractor of claim 1, wherein the non-contract EEG sensors comprise a mosfet.

3. A brain retractor configured to monitor a condition of a patient during a surgical procedure on a brain, the brain retractor system comprising:
   a brain surgery retractor blade configured to retract at least a portion of the patient's brain during the surgical procedure;
   a plurality of pressure sensors with continuous output disposed on said retractor blade, each pressure sensor configured to provide an indication of a pressure exerted against said pressure sensor;
   a plurality of EEG sensors disposed within the plurality of pressure sensors:
   a software controlled processor in communication with said pressure sensors to receive signals from said pressure sensors and that processes said signals to provide an indication of the pressure exerted on the brain when the retractor is in use;
and
   a display screen in communication with the software controlled processor.

4. The brain retractor of claim 3, wherein the EEG sensors are configured to measure capacitive electrical changes.

5. The brain retractor of claim 3, wherein the EEG sensors are configured to measure electrical signals associated with the patient's brain without being in physical contact with the patient's brain.

6. The brain retractor of claim 3, further comprising a temperature sensor.

7. A non-contact electrode for measuring the EEG in a patient, the electrode comprising:
   a first non-contact sensing portion configured to sense an indication of a biopotential of a first portion of a patient without contact with the patient;
   a second non-contact sensing portion configured to sense an indication of second biopotential of a second portion of a patient without contact with the patient;
   circuitry configured to use said first indication of a biopotential and said second indication of a biopotential to determine an indication of the EEG in a patient, wherein at least one of the non-contact sensing portions is disposed within a pressure sensor.

8. The non-contact electrode of claim 7, wherein the circuitry comprises a transistor.

9. The non-contact electrode of claim 8, wherein the circuitry comprises a mosfet.

10. The non-contact electrode of claim 7, wherein the first and second portions of the patient comprise portions of the patient's brain.

11. A method of measuring an EEG signal in a patient without contacting the patient with the EEG sensor while measuring the pressure exerted by a brain retractor, the method comprising:
- locating a non-contact EEG sensor disposed within a pressure sensor proximal a measurement site of a patient;
- sensing signals representative of EEG activity at the measurement site of the patient without contacting the measurement site of the patient with the EEG sensor disposed within the pressure sensor; and
- providing an indication of an EEG measurement.

12. The method of claim 11, wherein locating a non-contact EEG sensor disposed within a pressure sensor proximal a measurement site of a patient comprises locating a non-contact EEG sensor disposed within the pressure sensor comprised within a surgical instrument proximal a measurement site of a patient, wherein the instrument contacts the measurement site but the EEG sensor does not.

13. The method of claim 12, further comprising determining an amount of pressure exerted on the measurement site by the instrument.

14. The method of claim 13, wherein determining the amount of pressure exerted on the measurement site comprises using a plurality of pressure sensors on the surgical instrument.

15. The method of claim 11, further comprising determining an indication of the temperature of the measurement site.

16. The method of claim 11, further comprising alerting a caregiver to a condition of the patient based on the indication of the EEG measurement.

* * * * *